(12) United States Patent
Dixit et al.

(10) Patent No.: US 6,747,138 B1
(45) Date of Patent: Jun. 8, 2004

(54) METHODS AND COMPOSITIONS FOR REGULATING FAS-ASSOCIATED APOPTOSIS

(75) Inventors: Vishva M. Dixit, Ann Arbor, MI (US); Karen O'Rourke, Ann Arbor, MI (US)

(73) Assignee: Regents of the University of Michigan, Ann Arbor, MI (US)

( * ) Notice: Subject to any disclaimer, the term of this patent is extended or adjusted under 35 U.S.C. 154(b) by 257 days.

(21) Appl. No.: 08/844,691

(22) Filed: Apr. 21, 1997

Related U.S. Application Data

(63) Continuation of application No. 08/416,379, filed on Apr. 3, 1995, now abandoned.

(51) Int. Cl.$^7$ .................... C07H 21/04; C07K 14/435
(52) U.S. Cl. .................................. 536/23.5; 530/300
(58) Field of Search ..................... 435/69.1, 320.1, 435/325; 735/16; 536/23.5; 530/350, 300

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91.2 |
| 4,754,065 A | 6/1988 | Levenson et al. | 562/564 |
| 4,800,159 A | 1/1989 | Mullis et al. | 435/91.2 |
| 5,258,454 A | 11/1993 | Berg et al. | 525/54.11 |
| 5,674,734 A | 10/1997 | Leder et al. | 435/252.3 |

FOREIGN PATENT DOCUMENTS

| | | |
|---|---|---|
| WO | WO 93/25685 | 12/1993 |
| WO | WO 93/25694 | 12/1993 |
| WO | 9418317 | * 8/1994 |
| WO | WO 94/21817 | 9/1994 |
| WO | WO 94/24297 | 10/1994 |
| WO | WO 94/25621 | 11/1994 |
| WO | WO 94/27583 | 12/1994 |
| WO | WO 95/31544 | 11/1995 |
| WO | WO 96/01642 | 1/1996 |
| WO | WO 96/18641 | 6/1996 |
| WO | WO 96/20721 | 7/1996 |
| WO | WO 96/36698 | 11/1996 |
| WO | WO 96/40713 | 12/1996 |
| WO | WO 97/18313 | 5/1997 |
| WO | WO 98/03648 | 1/1998 |

OTHER PUBLICATIONS

Maekawa et al. FEBS Letters. vol. 337, pp. 200–206. Molecular cloning of a novel protein–tyrosine phosphatase containing a membrane–binding domain and GLGF repeats, Jan. 10, 1993.*

Marshall, et al. EMBO J. vol. 9(13): pp. 4391–4398, GENEBANKa101, Accession No. X55439, 1990.*

Allison et al., "The yin and yang of T cell costimulation" *Science* (1995) 270:932–933.

Barres et al., "Cell death and control of cell survival in the oligodendrocyte lineage" Cell (1992) 70:31–46.

Beidler et al., "The baculovirus p35 protein inhibits fas– and tumor necrosis factor–induced apoptosis" *J. Biol. Chem.* (1995) 270:16526–16528.

Blau et al., "Molecular medicine: Gene therapy—a novel form of drug delivery" *N. Eng. J. Med.* (1995) 333:1204–1207.

Bose et al., "Ceramide synthase mediates daunorubicin–induced apoptosis: An alternative mechanism for generating death signals" *Cell* (1995) 82:405–414.

Boudreau et al., "Suppression of ICE and apoptosis in mammary epithelial cells by extracellular matrix" *Science* (1995) 267:891–893.

Boulakia et al., "Bcl–2 and adenovirus E1B 19 kDa protein prevent E1A–induced processing of CPP32 and cleavage of poly(ADP–ribose) polymerase" *Oncogene* (1996) 12:529–535.

Bump et al., "Inhibition of ICE family proteases by baculovirus antiapoptotic protein p35" *Science* (1995) 269:1885–1888.

Casciola–Rosen et al., "Specific cleavage of the 70–kDa protein component of the U1 small nuclear ribonucleoprotein is a characteristic biochemical feature of apoptotic cell death" *J. Biol. Chem.* (1994) 269:30757–30760.

Chinnaiyan et al., "FADD/MORT1 is a common mediator of CD95 (Fas/APO–1) and tumor necrosis factor receptor–induced apoptosis" *J. Biol. Chem.* (1996) 271:4961–4965.

Chinnaiyan et al., "Molecular ordering of the cell death pathway" *J. Biol. Chem.* (1996) 271:4573–4576.

Clem et al., "Prevention of apoptosis by a baculovirus gene during infection of insect cells" *Science* (1991) 254:1388–1390.

Clem et al., "Control of programmed cell death by the baculovirus genes p35 and iap" *Mol. & Cell. Biol.* (1994) 14:5212–5222.

Cleveland et al., "Contenders in FasL/TNF death signaling" *Cell* (1995) 81:479–482.

Correll et al., "Production of human glucocerebrosidase in mice after retroviral gene transfer into multipotential hematopoietic progenitor cells" Proc. Natl. Acad. Sci. USA (1989) 86:8912–8916.

Darmon et al., "Activation of the apoptotic protease CPP32 by cytotoxic T–cell–derived granzyme B" *Nature* (1995) 377:446–448.

Dixit et al., "Tumor necrosis factor–α induction of novel gene products in human endothelial cells including a macrophage–specific chemotaxin" J. Biol. Chem. (1990) 265:2973–2978.

(List continued on next page.)

Primary Examiner—David S. Romeo
(74) *Attorney, Agent, or Firm*—Medlen & Carroll, LLP

(57) ABSTRACT

This invention provides a novel purified mammalian protein designated FADD having the ability to bind the cytoplasmic region or domain of the Fas receptor. Also provided are nucleic acid molecules that encode the mammalian protein which binds the intracellular domain of Fas as well as methods for using the proteins and nucleic acid molecules.

2 Claims, 17 Drawing Sheets

OTHER PUBLICATIONS

Duan et al., "ICE–LAP3, a novel mammalian homologue of the *Caenorhabditis elegans* cell death protein CED–3 is activated during Fas– and tumor necrosis factor–induced apoptosis" *J. Biol. Chem.* (1996) 271:1621–1625.

Ellis et al., "Genetic control of programmed cell death in the nematode *C. elegans*" *Cell* (1986) 44:817–829.

Faucheu et al., "A novel human protease similar to the interleukin–1β converting enzyme induces apoptosis in transfected cells" *EMBO J.* (1995) 14:1914–1922.

Fernandes–Alnemri et al., "CPP32, a novel human apoptotic protein with homology to *Caenorhabditis elegans* cell death protein Ced–3 and mammalian interleukin–1β–converting enzyme" *J. Biol. Chem.* (1994) 269:30761–30764.

Fernandes–Alnemri et al., "Mch2, a new member of the apoptotic Ced–3/Ice cysteine protease gene family" *Cancer Res.* (1995) 55:2737–2742.

Fernandes–Alnemri et al., "Mch3, a novel human apoptotic cysteine protease highly related to CPP32" *Cancer Res.* (1995) 55:6045–6052.

Finkel et al., "Apoptosis occurs predominantly in bystander cells and not in productively infected cells of HIV– and SIV–infected lymph nodes" *Nature Med.* (1995) 1:129–134.

Fisher et al., "Dominant interfering Fas gene Mutations impair apoptosis in a human autoimmune lymphoproliferative syndrome" *Cell* (1995) 81:935–946.

Gagliardini et al., "Prevention of vertebrate neuronal death by the crmA gene" *Science* (1994) 263:826–828.

Golstein et al., "Homology between reaper and the cell death domains of Fas and TNFR1" *Cell* (1995) 81:185–186.

Gooding, "Virus proteins that counteract host immune defenses" *Cell* (1992) 71:5–7.

Hanabuchi et al., "Fas and its ligand in a general mechanism of T–cell–mediated cytotoxicity" *Proc. Natl. Acad. Sci. USA* (1994) 91:4930–4934.

Henderson et al., "Epstein–Barr virus–coded BHRF1 protein, a viral homologue of Bcl–2, protects human B cells from programmed cell death" *Proc. Natl. Acad. Sci. USA* (1993) 90:8479–8483.

Hengartner, "Life and death decisions: ced–9 and programmed cell death in *Caenorhabditis elegans*" *Science* (1995) 270:931.

Hsu et al., "TRADD–TRAF2 and TRADD–FADD interactions define two distinct TNF receptor 1 signal transduction pathways" *Cell* (1996) 84:299–308.

Hynes et al., "A target for tumour–directed therapy" *Nature Medicine* (1995) 1:631–632.

Itoh et al., "Effect of bcl–2 on Fas antigen–mediated cell death" *J. Immunol.* (1993) 151:621–627.

Iwai et al., "Differential expression of bcl–2 and susceptibility to anti–Fas–mediated cell death in peripheral blood lymphocytes, monocytes, and neutrophils" *Blood* (1994) 84:1201–1208.

Ju et al., "Participation of target Fas protein in apoptosis pathway induced by CD4$^+$ Th1 and CD8$^+$ cytotoxic T cells" *Proc. Natl. Acad. Sci. USA* (1994) 91:4185–4189.

Kägi et al., "Fas and perforin pathways as major mechanisms of T cell–mediated cytotoxicity" *Science* (1994) 265:528–530.

Kamens et al., "Identification and characterization of ICH–2, a novel member of the interleukin–1β–converting enzyme family of cysteine proteases" *J. Biol. Chem.* (1995) 270:15250–15256.

Kaufmann et al., "Specific proteolytic cleavage of poly(AD-P–ribose)polymerase: An early marker of chemotherapy–induced apoptosis" *Cancer Res.* (1993) 53:3976–3985.

King et al., "Signaling for death of lymphoid cells" *Current Opinion in Immunol.* (1993) 5:368–373.

Komiyama et al., "Inhibition of interleukin–1β converting enzyme by the cowpox virus serpin CrmA" *J. Biol. Chem.* (1994) 269:19331–19337.

Kuby, "Immunology" W.H. Freeman and Company, N.Y. (1992) 257.

Kuida et al., "Altered cytokine export and apoptosis in mice deficient in interleukin–1β converting enzyme" *Science* (1995) 267:2000–2003.

Kumar et al., "Protection from tumor necrosis factor–mediated cytolysis by overexpression of plasminogen activator inhibitor type–2" *J. Biol. Chem.* (1991) 266:20960–20964.

Kumar et al., "Induction of apoptosis by the mouse Nedd2 gene, which encodes a protein similar to product of the *Caenorhabditis elegans* cell death gene ced–3 and the mammalian IL–1β–converting enzyme" *Genes & Devel.* (1994) 8:1613–1626.

Laherty et al. "Human T cell leukemia virus Type I tax and phorbol 12–myristate 13–acetate induce expression of the A20 zinc finger protein by distinct mechanisms involving nuclear factor KB" J. Biol. Chem. (1993) 268:5032–5039.

Lazebnik et al., "Cleavage of poly(ADP–ribose)polymerase by a proteinase with properties like ICE" *Nature* (1994) 371:346–347.

Li et al., "Mice deficient in IL–1β–converting enzyme are defective in production of mature IL–1β and resistant to endotoxic shock" *Cell* (1995) 80:401–411.

Liston et al., "Suppression of apoptosis in mammalian cells by NAIP and a related family of IAP genes" *Nature* (1996) 379:349–353.

Margolick et al., "Failure of T–cell homeostatis preceding AIDS in HIV–1 infection" *Nature Medicine* (1995) 1:674–680.

Martin et al., "Biochemical characterizaton of programmed cell death in NGF–deprived sympathetic neurons" *J. Neurobiol.* (1992) 23:1205–1220.

Martinou et al., "Viral proteins E1B19K and p35 protect sympathetic neurons from cell death induced by NGF deprivation" *J. Cell Biol.* (1995) 128:201–208.

McElvaney et al., "IL–6 release and airway administration of human CFTR cDNA adenovirus vector" *Nature Medicine* (1995) 1:182–184.

Miller et al., "Improved retroviral vectors for gene transfer and expression" BioTechniques (1989) 7:980–990.

Milner, "DNA damage, p53 and anticancer therapies" *Nature Medicine* (1995) 1:879–880.

Morrison, et al. "Direct Activation of the Serine/Threonine Kinase Activity of Raf–1 through Tyrosine Phosphorylation by the PDGF β–Receptor" *Cell* (1989) 58:649–57.

Moss, "Poxviridae and their reproduction" Virology, 2nd ed., Fields, B.N. et al., eds., Raven Press, New York (1990) Chapter 74, pp. 2079–2111.

Munday et al., "Molecular cloning and pro–apoptotic activity of ECE$_{rel}$II and ICE$_{rel}$III, members of the ICE/CED–3 family of cysteine proteases" *J. Biol. Chem.* (1995) 270:15870–15876.

Na et al., "D4–GDI, a substrate of CPP32, is proteolyzed during Fas–induced apoptosis" *J. Biol. Chem.* (1996) 271:11209–11213.

Nicholson, "ICE/CED3–like proteases as therapeutic targets for the control of inappropriate apoptosis" *Nature Biotechnol.* (1996) 14:297–301.

Nicholson et al., "Identification and inhibition of the ICE/CED–3 protease necessary for mammalian apoptosis" *Nature* (1995) 376:37–43.

Orkin, et al. "Report and recommendation of the panel to assess the NIH investment in research on gene therapy" (1995).

Paigen, "A miracle enough: the power of mice" *Nature Medicine* (1995) 1:215–220.

Pantaleo et al., "Apoptosis in HIV infection" *Nature Med.* (1995) 1:118–120.

Peter et al., "CD95 (APO–1/FAS)–associating signalling proteins" *Cell Death and Differentiation* (1996) 3:161–170.

Pickup et al., "Hemorrhage in lesions caused by cowpox virus is induced by a viral protein that is related to plasma protein inhibitors of serine proteases" Proc. Natl. Acad. Sci. (1986) 83:7698–7702.

Rabizadeh et al., "Expression of the baculovirus p35 gene inhibits mammalian neural cell death" *J. Neurochem.* (1993) 61:2318–2321.

Ray et al., "Viral Inhibition of inflammation: Cowpox virus encodes an inhibitor of the interleukin–1β converting enzyme" Cell (1992) 69:597–604.

Roederer, "T–cell dynamics of immunodeficiency" *Nature Medicine* (1995) 1:621–622.

Rothe et al., "TRAF2–mediated activation of NF–kB by TNF receptor 2 and CD40" *Science* (1995) 269:1424–1427.

Rothe et al., "The TNFR2–TRAF signaling complex contains two novel proteins related by baculoviral inhibitor of apoptosis proteins" *Cell* (1995) 83:1243–1252.

Roy et al., "The gene for neuronal apoptosis inhibitory protein is partially deleted in individuals with spinal muscular atrophy"*Cell* (1995) 80:167–178.

Ruggiero et al., "Protection from tumor necrosis factor cytotoxicity by protease inhibitors" *Cellular Immunol.* (1987) 107:317–325.

Schlegel et al., "CPP32/apopain is a key interleukin 1β converting enzyme–like protease involved in Fas–mediated apoptosis" *J. Biol. Chem.* (1996) 271:1841–1844.

Smith et al. "CrmA expression in T lymphocytes of transgenic mice inhibits CD95 (Fas/APO–1)–transduced apoptosis, but does not cause lymphadenopathy or autoimmune disease" *The EMBO Journal* (1996) 15:5167–5176.

Soares, GenBank Accension No. T10341 (1994).

Stalder et al., "Fas antigen is the major target nolecule for CD4$^+$ T cell–mediated cytotoxicity" *J. Immunol.* (1994) 152:1127–1133.

Stinchcomb, "Constraining the cell cycle: Regulating cell division and differentiation by gene therapy" *Nature Medicine* (1995) 1:1004–1006.

Strasser, "Death of a T cell" *Nature* (1995) 373:385–386.

Suffys et al., "Involvement of a serine protease in tumour–necrosis–factor–mediated cytotoxicity" *Eur. J. Biochem.* (1988) 178:257–265.

Sugimoto et al., "Baculovirus p35 prevents developmentally programmed cell death and rescues a ced–9 mutant in the nematode *Caenorhabditis elegans*" *EMBO J.* (1994) 13:2023–2028.

Tamura et al., "An IRF–1–dependent pathway of DNA damage–induced apoptosis in mitogen–activated T lymphocytes" *Nature* (1995) 376:596–599.

Tanaka et al., "Fas ligand in human serum" *Nature Medicine* (1996) 2:317–322.

Tartaglia et al., "A novel domain within the 55 kd TNF receptor signals cell death" Cell (1993) 74:845–853.

Tewari et al., "CrmA–inhibitable cleavage of the 70–kDa protein component of the U1 small nuclear ribonucleoprotein during Fas– and tumor necrosis factor–induced apoptosis" *J. Biol. Chem.* (1995) 270:18738–18741.

Tewari et al., "Yama/CPP32β, a mammalian homolog of CED–3, is a CrmA–inhibitable protease that cleaves the death substrate poly(ADP–ribose) polymerase" *Cell* (1995) 81:801–809.

vanBockxmeer et al., "Premature ischaemic heart disease and the gene for coagulation factor V" *Nature Medicine* (1995) 1:185.

Verheij et al., "Requirement for ceramide–initiated SAPK/JNK signalling in stress–induced apoptosis" *Nature* (1996) 380:75–79.

Vermes et al., "Apoptosis and programmed cell death in health and disease" (1994) Academic Press, Inc., pp. 177–246.

Vito et al., Interfering with apoptosis: $Ca^{2+}$–binding protein ALG–2 and Alzheimer's disease gene ALG–3 *Science* (1996) 271:521–525.

Walker et al., "Crystal structure of the cysteine protease interleukin–1β–converting enzyme: A $(p20/p10)_2$ homodimer" *Cell* (1994) 78:343–352.

Wang et al., "Ich–1, an Ice/ced–3–related gene, encodes both positive and negative regulators of programmed cell death" *Cell* (1994) 78:739–750.

Wang et al., "Cleavage of sterol regulatory element binding proteins (SREBPs) by CPP32 during apoptosis" *EMBO J.* (1996) 15:1012–1020.

Westendorp et al., "Sensitization of T cells to CD95–mediated apoptosis by HIV–1 Tat and gp120" *Nature* (1995) 375:497–500.

White, "Regulation of apoptosis by the transforming genes of the DNA tumor virus adenovirus (43631)" *P.S.E.B.M.* (1993) 204:30–39.

Whyte et al., "The last cut is the deepest" *Nature* (1995) 376:17–18.

Williams et al., "Apoptotic cell death induced by intracellular proteolysis" *J. Immunol.* (1994) pp. 4247–4255.

Wilson et al., "Structure and mechanism of interleukin–1β converting enzyme" *Nature* (1994) 370:270–275.

Woo, "Apoptosis and loss of renal tissue in polycystic kidney diseases" *N. Eng. J. Med.* (1995) 333:18–25.

Wu et al., "Interaction of the erythropoietin and stem–cell–factor receptors" *Nature* (1995) 377:242–246.

Xue et al., "Inhibition of the *Caenorhabditis elegans* cell–death protease CED–3 by a CED–3 cleavage site in baculovirus p35 protein" *Nature* (1995) 377:248–251.

Zheng et al., "Induction of apoptosis in mature T cells by tumour necrosis factor" *Nature* (1995) 377:348–351.

EMBL Database, Accension No. PIR P9135 Kotwal JG, Moss B (Jan. 12, 1990).

Daniel et al. (1994) "Mapping of linear antigenic sites on the S glycoprotein of a nuurotropic murine coronavirus with synthetic peptides: a combination of nine prediction algorithms fails to identify relevant epitopes and peptide immunogenicity is drastically influenced by the nature of the protein carrier" *Virology* 202:549–9.

Sambrook et al.(1989) *Chapter 17 Expression of Cloned Genes in Escherichia coli,* Molecular Cloning: A Laboratory Manual, 2nd Ed., vols. 1, 2 and 3, Cold Harbor Laboratory Press, Cold Spring Harbor, NY.

Boldin et al., "A novel protein that interacts with the death domain of Fas/APO1 contains a sequence motif related to the death domain" *J. Biol. Chem.* (1995) 270:7795–7798.

Hsu et al., "The TNF receptor 1–associated protein TRADD signals cell death and NF–κB activation" *Cell* (1995) 81:495–504.

Chinnaiyan et al., "FADD, a novel death domain–containing protein, interacts with the death domain of Fas and initiates apoptosis" *Cell* (1995) 81:505–512.

Stanger et al., "RIP: a novel protein containing a death domain that interacts with Fas/APO–1 (CD95) in yeast and causes cell death" *Cell* (1995) 81:513–523.

Kischkel et al., "Cytotoxicity–dependent APO–1 (Fas/CD95)–associated proteins form a death–inducing signaling complex (DISC) with the receptor" *EMBO J.* (1995) 14:5579–5588.

Itoh et al., "A novel protein domain required for apoptosis" *J. Biol. Chem.* (1993) 268:10932–10937.

Rathmell et al. "Expansion or Elimination of B Cells In Vivo: Dual Roles for CD40– and Fas (CD95)–Ligands Modulated by the B Cell Antigen Receptor" *Cell* (1996) 87:319–329.

Strand et al. "Lymphocyte apoptosis induced by CD95 (APO–1/Fas) ligand–expressing tumor cell—A mechanism of immune evasion?" *Nature Medicine* (1996) 2(12):1361–1366.

Tewari et al. "CrmA, a poxvirus–encoded serpin, inhibits cytotoxic T–lymphocyte–mediated apoptosis" *J. Biol. Chem.* (1995) 270(39):22705–22708.

Vaux et al., "An evolutionary perspective on apoptosis" *Cell* (1994) 76:777–779.

Ellis et al., "Mechanisms and functions of cell death" *Ann. Rev. Cell Biol.* (1991) 7:663–698.

Tomei et al., "Apoptosis: The Molecular Basis of Cell Death" *Current Communications in Cell & Molecular Biology 3* (1991) Cold Spring Harbor Press, New York. A title page and table of contents are enclosed herewith.

Tomei et al., "Apoptosis II: The Molecular Basis of Cell Death" *Current Communications in Cell and Molecular Biology 8* (1994) Cold Spring Harbor Press, New York. A title page and table of contents are enclosed herewith.

Duvall et al., "Death and the cell" *Immunol. Today* (1986) 7:115–119.

Cohen, "Apoptosis" *Immunol. Today* (1993) 14:126–130.

Brunner et al., "Cell–autonomous Fas (CD95)/Fas–ligand interaction mediates activation–induced apoptosis in T–cell hybridomas" *Nature* (1995) 373:441–444.

Dhein et al., "Autocrine T–cell suicide mediated by APO–11(Fas/CD95)" *Nature* (1995) 373:438–441.

Ju et al., "Fas(CD95)/FasL interactions required for programmed cell death after T–cell activation" *Nature* (1995) 373:444–448.

Itoh et al., "The polypeptide encoded by the cDNA for human cell surface antigen Fas can mediate apoptosis" *Cell* (1991) 66:233–243.

Tewari et al., "Fas– and tumor necrosis factor–induced apoptosis is inhibited by the poxvirus crmA gene product" *J. Bio. Chem.* (1995) 270:3255–3260.

Yuan et al., "The C. elegans cell death gene ced–3 encodes a protein similar to mammalian interleukin–1β–converting enzyme" *Cell* (1993) 75:641–652.

Cerretti et al., "Molecular cloning of the interleukin–1β converting enzyme" *Science* (1992) 256:97–100.

Thornberry et al., "A novel heterodimeric cysteine protease is required for interleukin–1β processing monocytes" *Nature* (1992) 356:768–774.

Miura et al., "Induction of apoptosis in fibroblasts by IL–1β–converting enzyme, a mammalian homolog of the C. elegans cell death gene ced–3" *Cell* (1993) 75:653–660.

Baglioni, "Mechanisms of cytotoxicity, cytolysis, and growth stimulation by TNF" *Tumor Necrisis Factors. The Molecules and Their Emerging Role in Medicine* (1992) B. Beutler, M.D., ed., Raven Press, New York. A title page and table of contents are enclosed herewith.

Yonehara et al.. "A cell–killing monoclonal antibody (Anti–Fas) to a cell surface antigen co–downregulated with the receptor of tumor necrosis factor" *J. Exp. Med.* (1989) 169:1747–1756.

Trauth et al., "Monoclonal antibody–mediated tumor regression by induction of apoptosis" *Science* (1989) 245:301–305.

Watanabe–Fukunaga et al., "Lymphoproliferation disorder in mice explained by defects in Fas antigen that mediates apoptosis" *Nature* (1992) 356:314–317.

Tartaglia et al., "Two TNF receptors" *Immunol. Today* (1992) 13:151–153.

Boldin et al., "Self–association of the 'death domains' of the p55 tumor necrosis factor (TNF) receptor and Fas/APO1 prompts signaling for TNF and Fas/APO1 effects" *J. Biol. Chem.* (1995) 270:387–391.

Song, "Aggregation of the intracellular domain of the Type I tumor necrosis factor receptor defined by the two–hybrid system" *J. Biol Chem.* (1994) 269:22492–22495.

Bordignon et al., "Retroviral vector–mediated high–efficiency expression of adenosine deaminase (ADA) in hematopoietic long–term cultures of ADA–deficient marrow cells" *Proc. Natl. Acad. Sci. USA* (1989) 86:6748–6752.

Culver et al., "Lymphocytes as cellular vehicles for gene therapy in mouse and man" *Proc. Natl. Acad. Sci. USA* (1991) 88:3155–3159.

Rill et al., "An approach for the analysis of relapse and marrow reconstitution after autologous marrow transplantation using retrovirus–mediated gene transfer" *Blood* (1992) 79:2694–2700.

Anderson, "Human gene therapy" *Science* (1992) 256:808–813.

Steplewski et al., "Isolation and characterization of anti––monosialoganglioside monoclonal antibody 19–9 class–switch variants" *Proc. Natl. Acad. Sci. USA* (1985) 82:8653–8657.

Spira et al., "The identification of monoclonal class switch variants by Sib selection and an ELISA assay" *J. Immunol. Meth.* (1984) 74:307–315.

Oi et al., "Chimeric antibodies" *BioTechniques* (1986) 4:214–221.

Herlyn et al., "Anti–idiotypic antibodies bear the internal image of a human tumor antigen" *Science* (1986) 232:100–102.

Spriggs et al., "Tumor necrosis factor expression in human epithelial tumor cell lines" *J. Clin. Invest.* (1988) 81:455–460.

Watanabe–Fukunaga et al., "The cDNA structure, expression, and chromosomal assignment of the mouse Fas antigen" *J. Immun.* (1992) 148:1274–1279.

Owen–Schaub et al., "Anti–Fas on nonhematopoietic tumors: Levels of Fas/APO–1 and bcl–2 are not predictive of biological responsiveness" *Cancer Res.* (1994) 54:1580–1586.

Opipari, Jr. et al., "The A20 zinc finger protein protects cells from tumor necrosis factor cytotoxicity" *J. Biol. Chem.* (1992) 267:12424–12427.

Lum et al., "Coactivation with anti–CD28 monoclonal antibody enhances anti–CD3 monoclonal antibody–induced proliferation and IL–2 synthesis in T cells from autologous bone marrow transplant recipients" *Bone Marrow Transplantation* (1993) 12:565–571.

Hu et al., "A novel RING finger protein interacts with the cytoplasmic domain of CD40" *J. Biol Chem.* (1994) 269:30069–30072.

Higuchi et al., "A general method of in vitro preparation and specific mutagenesis of DNA fragments: study of protein and DNA interactions" *Nucl. Acids Res.* (1988) 16:7351–7367.

Ron et al., "pGSTag—a versatile bacterial expression plasmid for enzymatic labeling of recombinant proteins" *BioTechniques* (1992) 13:866–869.

Studier, "Use of bacteriophage T7 lysozyme to improve an inducible T7 expresssion system" *J. Mol. Biol.* (1991) 219:37–44.

Harper et al., "The p21 Cdk–interacting protein Cip1 is a potent inhibitor of G1 cyclin–dependent kinases" *Cell* (1993) 75:805–816.

O'Rourke et al., "Thrombospondin 1 and Thrombospondin 2 are expressed as both homo– and heterotrimers" *J. Biol. Chem.* (1992) 267:24921–24924.

Peters et al., "Ankyrins: Structure and function in normal cells and hereditary spherocytes" *Semininars in Hematol.* (1993) 30:85–118.

Clement et al., "Fas and tumor necrosis factor receptor–mediated cell death: Similarities and distinctions" *J. Exp. Med.* (1994) 180:557–567.

* cited by examiner

```
CTCTAAGGTTCGGGGTGGAATCCTTGGGCCGCTGGGCAAGCGGCGAGACCTGGCCAGGCCAGCGGAGCCGAGGACAGAGGGCGCACGGAGGGCCGGGC   100

CGCAGCCCCGCCGCTTGCAGACCCCGCC    ATG GAC CCG TTC CTG CTG GTG CTG CAC TCG GTG TCG TCC AGC CTG TCG AGC
                                Met Asp Pro Phe Leu Leu Val Leu His Ser Val Ser Ser Ser Leu Ser Ser
                                                                                                Clone
              200 Clone 18
AGC GAG CTG ACC GAG CTC AAG TTC CTA TGC CTC GGG CGC GTG GGC AAG CTG GAG CGC GTG CAG AGC GGC
Ser Glu Leu Thr Glu Leu Lys Phe Leu Cys Leu Gly Arg Val Gly Lys Leu Glu Arg Val Gln Ser Gly 300
CTA GAC CTC TTC ATG CTG CTG GAG CAG AAC GAC CTG GAG CCC GGG CAC ACC GAG CTC CGC GAG CTG CTC
Leu Asp Leu Phe Ser Met Leu Leu Glu Gln Asn Asp Leu Glu Pro Gly His Thr Glu Leu Arg Glu Leu Leu 400
GCC TCC CTG CGG CGC CAC GAC CTG CGG CGC GTC GAC GAC TTC GAG GCG GGG GCG GCG GCC GGG GCC CCT
Ala Ser Leu Arg Arg His Asp Leu Arg Arg Val Asp Asp Phe Glu Ala Gly Ala Ala Ala Gly Ala Ala Pro GGG GAA GAC CTG TGT GCA GCA TTT AAC GTC ATA TGT GAT AAT GTG GGG AAA GAT TGG AGA AGG CTG GCT CGT
Gly Glu Asp Leu Cys Ala Ala Phe Asn Val Ile Cys Asp Asn Val Gly Lys Asp Trp Arg Arg Leu Ala Arg 500
CAG CTC AAA GTC TCA GAC ACC AAG ATC GAC AGC ATC GAG GAC AGA TAC CCC CGC AAC CTG ACA GAG CGT GTG CGG
Gln Leu Lys Val Ser Asp Thr Lys Ile Asp Ser Ile Glu Asp Arg Tyr Pro Arg Asn Leu Thr Glu Arg Val Arg
```

FIG. 2A

GAG TCA CTG AGA ATC TGG AAG AAC ACA GAG AAG GAG AAC GCA ACA GTG GCC CAC CTG GTG GGG GCT CTC AGG TCC
Glu Ser Leu Arg Ile Trp Lys Asn Thr Glu Lys Glu Asn Ala Thr Val Ala His Leu Val Gly Ala Leu Arg Ser

TGC CAG ATG AAC CTG GTG GCT GAC CTG GTA CAA GAG GTT CAG CAG GCC CGT GAC CTC CAG AAC AGG AGT GGG GCC
Cys Gln Met Asn Leu Val Ala Asp Leu Val Gln Glu Val Gln Gln Ala Arg Asp Leu Gln Asn Arg Ser Gly Ala

ATG TCC CCG ATG TCA TGG AAC TCA GAC GCA TCT ACC TCC GAA GCG TCC TGATGGGCCGCTGCTTTGGCGCTGGTGGACCACAGGC
Met Ser Pro Met Ser Trp Asn Ser Asp Ala Ser Thr Ser glu Ala Ser *

ATCTACACAGCCTGGACTTTGGTTCTCTCCAGGAAGGTAGCCCAGCACTGTGAAGACCCAGCAGGAAGCCAGGCTGAGTGAGCCACAGACCACCTGCTTC

TGAACTCAAGCTGGCGTTTATTAATGCCTCTCCCGACCAGGCCCGGGCTTGGGCCCTGCACAGATATTTCCATTTCTTCCTCACTATGACACTGAGCAAGA

TCTTGTCTCCACTAAATGAGCTCCTGCGGGAGTAGTTGGAAAGTTGGAACCGTGTCCAGCACAGAAGGAATCTGTGCAGATGAGCAGTCACACTGTTACT

FIG. 2B

1100
CCACAGCGGAGGAGACCAGCTCAGAGGCCCAGGAATCGGGAGCGGAAGCAGAGAGGTTGGAGAACTGGGATTTGAACCCCCGCCATCCTTCACCAGAGCCCAT
1200
GCTCAACCACTGTGGGCGTTCCTGCCCCTGCAGTTGGCAGAAAGGATGTTTGTCCCATTCCTGGAGGCCACCGGGACAGACCTGGACACTAGGGTC
1300
AGGCGGGGTGCTGTGGTGGGGAGAGGCATGGCTGGGGTGGGGGTGGGGGAGACCTGGTTGGGCCGTGGTCCAGCTCTTGGCCCCTGTGTGAGTGAGTCTCC
1400
TCTTCTGAGACTGCTAAGTAGGGGTCCTGCAATTCTACAGTTCTTCTTACTGTTTGTATCAAAATCACTATCTTTCTGATAACAGAATTGCCAAGGCAGCGGG
1500
TCTTCCTTGTGAGGATTATGGGTCCTGCAATTCTACAGTTCTTCTTACTGTTTGTATCAAAATCACTATCTTTCTGATAACAGAATTGCCAAGGCAGCGGG
1600
ATCTCGTATCTTTAAAAAGCAGTCCTCTCTTATTCCTAAGGTAATCCTATTAAAA

FIG. 2C

```
hFADD   (111-145)  DWRRLARQLKVSDTKIDSIEDRYPRNLTERVRESL
rFas    (217-251)  DAKKFARQLKIPESKIDEIEHNSPQDAAAEQKIQLL
hFas    (228-262)  QVKGFVRKNGVNEAKIDEIKNDNVQDTAEQKVQLL
hTNFR-1 (341-375)  RWKEFVRRLGLSDHEIDRLELQNGRCLREAQYSML
                                   ↑ hFADD   (146-180)  RIWKNTEKENATVAHLVGALRSCQMNLVADLVQEV
rFas    (252-286)  QCWYQSHGKTGACQALIQGLRKANRCDIAEIQAM
hFas    (263-297)  RNWHQLHGKKEAYDTLIKDLKKANLCTLAEKIQTF
hTNFR-1 (376-410)  ATWRRRTPRREATLELLGRVLRDMDLLGCLEDIEE
```

FIG. 2D

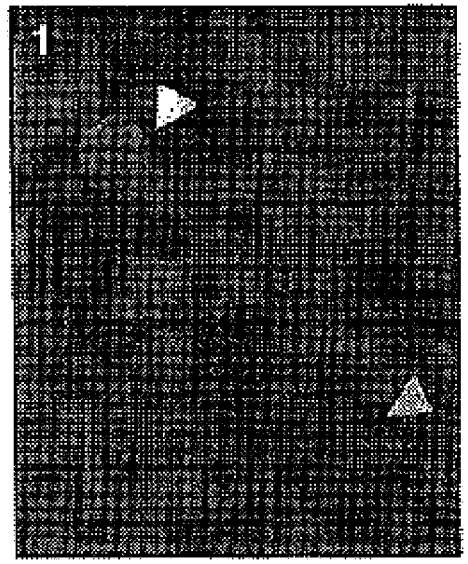
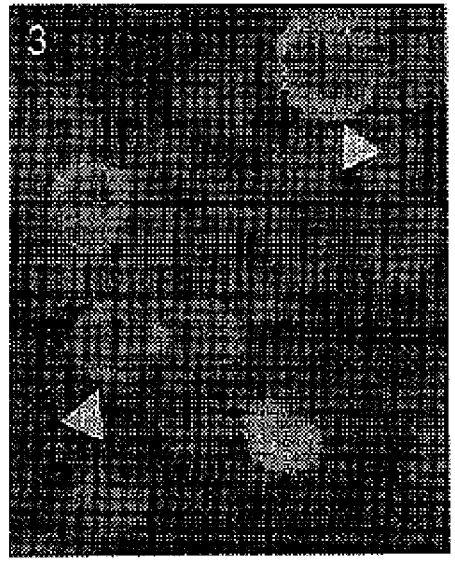
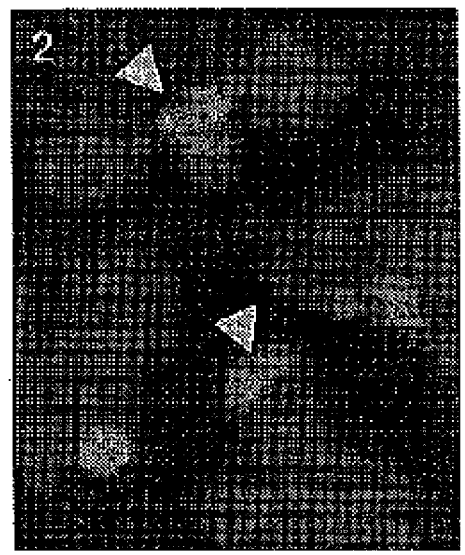
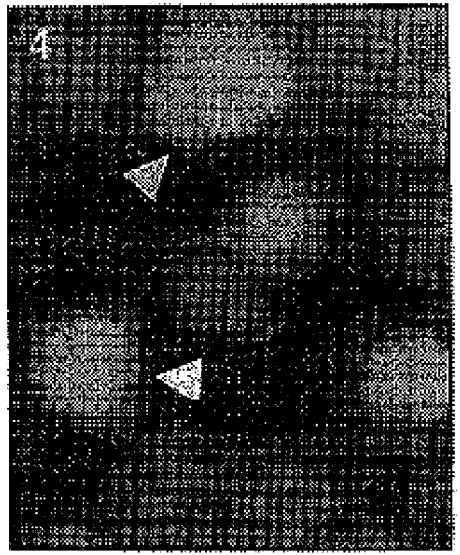
FIG. 7A

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
       (A) LENGTH: 1642 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 130..753

(ix) FEATURE:
       (A) NAME/KEY: misc_feature
       (B) LOCATION: 4..6
       (D) OTHER INFORMATION: /note= "An in-frame stop codon 130
           base pairs upstream of the initiator methionine"

(ix) FEATURE:
       (A) NAME/KEY: polyA_signal
       (B) LOCATION: 1636..1641
       (D) OTHER INFORMATION: /note= "Potential poly(A) adenylation
           signal"

(ix) FEATURE:
       (A) NAME/KEY: misc_feature
       (B) LOCATION: 198..753
       (D) OTHER INFORMATION: /note= "Clone-15; 5' end of FADD"

(ix) FEATURE:
       (A) NAME/KEY: misc_feature
       (B) LOCATION: 249..753
       (D) OTHER INFORMATION: /note= "Clone-8; 5' end of FADD"

(ix) FEATURE:
       (A) NAME/KEY: misc_feature
       (B) LOCATION: 460..660
       (D) OTHER INFORMATION: /note= "Death Domain of FADD"

(ix) FEATURE:
       (A) NAME/KEY: mutation
       (B) LOCATION: replace(490..492, "aay")
       (D) OTHER INFORMATION: /note= "For FADDmt: sequence is altered
           to either AAT or (ix) FEATURE:
       (A) NAME/KEY: misc_feature
       (B) LOCATION: group(250..753, 232..753)
       (D) OTHER INFORMATION: /note= "Codons can comprise C-terminal
           polypeptide fragme (ix) FEATURE:
       (A) NAME/KEY: misc_feature
       (B) LOCATION: 460..639
       (D) OTHER INFORMATION: /note= "death domain homology region"

(xi) SEQUENCE DESCRIPTION: SEQ ID NO:1:

```
CTCTAAAGGT TCGGGGGTGG AATCCTTGGG CCGCTGGGCA AGCGGCGAGA CCTGGCCAGG      60

GCCAGCGAGC CGAGGACAGA GGGCGCACGG AGGGCCGGGC CGCAGCCCCG GCCGCTTGCA     120

GACCCCGCC ATG GAC CCG TTC CTG GTG CTG CTG CAC TCG GTG TCG TCC        168
           Met Asp Pro Phe Leu Val Leu Leu His Ser Val Ser Ser
             1               5                  10

AGC CTG TCG AGC AGC GAG CTG ACC GAG CTC AAG TTC CTA TGC CTC GGG      216
Ser Leu Ser Ser Ser Glu Leu Thr Glu Leu Lys Phe Leu Cys Leu Gly
     15                  20                  25
```

```
CGC GTG GGC AAG CGC AAG CTG GAG CGC GTG CAG AGC GGC CTA GAC CTC          264
Arg Val Gly Lys Arg Lys Leu Glu Arg Val Gln Ser Gly Leu Asp Leu
 30              35                  40                  45

TTC TCC ATG CTG CTG GAG CAG AAC GAC CTG GAG CCC GGG CAC ACC GAG          312
Phe Ser Met Leu Leu Glu Gln Asn Asp Leu Glu Pro Gly His Thr Glu
             50                  55                  60

CTC CTG CGC GAG CTG CTC GCC TCC CTG CGG CGC CAC GAC CTG CTG CGG          360
Leu Leu Arg Glu Leu Leu Ala Ser Leu Arg Arg His Asp Leu Leu Arg
         65                  70                  75

CGC GTC GAC GAC TTC GAG GCG GGG GCG GCG GCC GGG GCC GCG CCT GGG          408
Arg Val Asp Asp Phe Glu Ala Gly Ala Ala Ala Gly Ala Ala Pro Gly
             80                  85                  90

GAA GAA GAC CTG TGT GCA GCA TTT AAC GTC ATA TGT GAT AAT GTG GGG          456
Glu Glu Asp Leu Cys Ala Ala Phe Asn Val Ile Cys Asp Asn Val Gly
         95                 100                 105

AAA GAT TGG AGA AGG CTG GCT CGT CAG CTC AAA GTC TCA GAC ACC AAG          504
Lys Asp Trp Arg Arg Leu Ala Arg Gln Leu Lys Val Ser Asp Thr Lys
110                 115                 120                 125

ATC GAC AGC ATC GAG GAC AGA TAC CCC CGC AAC CTG ACA GAG CGT GTG          552
Ile Asp Ser Ile Glu Asp Arg Tyr Pro Arg Asn Leu Thr Glu Arg Val
                130                 135                 140

CGG GAG TCA CTG AGA ATC TGG AAG AAC ACA GAG AAG GAG AAC GCA ACA          600
Arg Glu Ser Leu Arg Ile Trp Lys Asn Thr Glu Lys Glu Asn Ala Thr
            145                 150                 155

GTG GCC CAC CTG GTG GGG GCT CTC AGG TCC TGC CAG ATG AAC CTG GTG          648
Val Ala His Leu Val Gly Ala Leu Arg Ser Cys Gln Met Asn Leu Val
        160                 165                 170

GCT GAC CTG GTA CAA GAG GTT CAG CAG GCC CGT GAC CTC CAG AAC AGG          696
Ala Asp Leu Val Gln Glu Val Gln Gln Ala Arg Asp Leu Gln Asn Arg
175                 180                 185

AGT GGG GCC ATG TCC CCG ATG TCA TGG AAC TCA GAC GCA TCT ACC TCC          744
Ser Gly Ala Met Ser Pro Met Ser Trp Asn Ser Asp Ala Ser Thr Ser
190                 195                 200                 205

GAA GCG TCC TGATGGGCCG CTGCTTTGCG CTGGTGGACC ACAGGCATCT                  793
Glu Ala Ser

ACACAGCCTG GACTTTGGTT CTCTCCAGGA AGGTAGCCCA GCACTGTGAA GACCCAGCAG        853

GAAGCCAGGC TGAGTGAGCC ACAGACCACC TGCTTCTGAA CTCAAGCTGC GTTTATTAAT        913

GCCTCTCCCG CACCAGGCCG GGCTTGGGCC CTGCACAGAT ATTTCCATTT CTTCCTCACT        973

ATGACACTGA GCAAGATCTT GTCTCCACTA AATGAGCTCC TGCGGGAGTA GTTGGAAAGT       1033

TGGAACCGTG TCCAGCACAG AAGGAATCTG TGCAGATGAG CAGTCACACT GTTACTCCAC       1093

AGCGGAGGAG ACCAGCTCAG AGGCCCAGGA ATCGGAGCGA AGCAGAGAGG TGGAGAACTG       1153

GGATTTGAAC CCCGCCATC CTTCACCAGA GCCCATGCTC AACCACTGTG GCGTTCTGCT        1213

GCCCCTGCAG TTGGCAGAAA GGATGTTTTG TCCCATTTCC TTGGAGGCCA CCGGGACAGA       1273

CCTGGACACT AGGGTCAGGC GGGGTGCTGT GGTGGGGAGA GGCATGGCTG GGGTGGGGGT       1333

GGGGAGACCT GGTTGGCCGT GGTCCAGCTC TTGGCCCCTG TGTGAGTTGA GTCTCCTCTC       1393

TGAGACTGCT AAGTAGGGGC AGTGATGGTT GCCAGGACGA ATTGAGATAA TATCTGTGAG       1453

GTGCTGATGA GTGATTGACA CACAGCACTC TCTAAATCTT CCTTGTGAGG ATTATGGGTC       1513

CTGCAATTCT ACAGTTTCTT ACTGTTTTGT ATCAAAATCA CTATCTTTCT GATAACAGAA       1573

TTGCCAAGGC AGCGGGATCT CGTATCTTTA AAAAGCAGTC CTCTTATTCC TAAGGTAATC       1633

CTATTAAAA                                                              1642
```

(2) INFORMATION FOR SEQ ID NO:2:

(i) SEQUENCE CHARACTERISTICS:
        (A) LENGTH: 208 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asp Pro Phe Leu Val Leu Leu His Ser Val Ser Ser Ser Leu Ser
 1               5                  10                  15

Ser Ser Glu Leu Thr Glu Leu Lys Phe Leu Cys Leu Gly Arg Val Gly
                20                  25                  30

Lys Arg Lys Leu Glu Arg Val Gln Ser Gly Leu Asp Leu Phe Ser Met
            35                  40                  45

Leu Leu Glu Gln Asn Asp Leu Glu Pro Gly His Thr Glu Leu Leu Arg
        50                  55                  60

Glu Leu Leu Ala Ser Leu Arg Arg His Asp Leu Leu Arg Arg Val Asp
65                  70                  75                  80

Asp Phe Glu Ala Gly Ala Ala Ala Gly Ala Ala Pro Gly Glu Glu Asp
                85                  90                  95

Leu Cys Ala Ala Phe Asn Val Ile Cys Asp Asn Val Gly Lys Asp Trp
            100                 105                 110

Arg Arg Leu Ala Arg Gln Leu Lys Val Ser Asp Thr Lys Ile Asp Ser
        115                 120                 125

Ile Glu Asp Arg Tyr Pro Arg Asn Leu Thr Glu Arg Val Arg Glu Ser
130                 135                 140

Leu Arg Ile Trp Lys Asn Thr Glu Lys Glu Asn Ala Thr Val Ala His
145                 150                 155                 160

Leu Val Gly Ala Leu Arg Ser Cys Gln Met Asn Leu Val Ala Asp Leu
                165                 170                 175

Val Gln Glu Val Gln Gln Ala Arg Asp Leu Gln Asn Arg Ser Gly Ala
            180                 185                 190

Met Ser Pro Met Ser Trp Asn Ser Asp Ala Ser Thr Ser Glu Ala Ser
        195                 200                 205
```

(2) INFORMATION FOR SEQ ID NO:3:

(i) SEQUENCE CHARACTERISTICS:
        (A) LENGTH: 70 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 11
        (D) OTHER INFORMATION: /note= "Val is replaced by Asn for
            the point mutant hFADD"

(xi) SEQUENCE DESCRIPTION: SEQ ID NO:3:

```
Asp Trp Arg Arg Leu Ala Arg Gln Leu Lys Val Ser Asp Thr Lys Ile
 1               5                  10                  15

Asp Ser Ile Glu Asp Arg Tyr Pro Arg Asn Leu Thr Glu Arg Val Arg
                20                  25                  30

Glu Ser Leu Arg Ile Trp Lys Asn Thr Glu Lys Glu Asn Ala Thr Val
            35                  40                  45

Ala His Leu Val Gly Ala Leu Arg Ser Cys Gln Met Asn Leu Val Ala
```

```
            50                  55                  60
Asp Leu Val Gln Glu Val
 65                  70

(2) INFORMATION FOR SEQ ID NO:4:

(i) SEQUENCE CHARACTERISTICS:
        (A) LENGTH: 70 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 11
        (D) OTHER INFORMATION: /note= "Ile is replaced by Asn for
            the point mutant rFas"

(xi) SEQUENCE DESCRIPTION: SEQ ID NO:4:

Asp Ala Lys Lys Phe Ala Arg Gln His Lys Ile Pro Glu Ser Lys Ile
 1               5                  10                  15

Asp Glu Ile Glu His Asn Ser Pro Gln Asp Ala Ala Glu Gln Lys Ile
                20                  25                  30

Gln Leu Leu Gln Cys Trp Tyr Gln Ser His Gly Lys Thr Gly Ala Cys
            35                  40                  45

Gln Ala Leu Ile Gln Gly Leu Arg Lys Ala Asn Arg Cys Asp Ile Ala
            50                  55                  60

Glu Glu Ile Gln Ala Met
 65                  70

(2) INFORMATION FOR SEQ ID NO:5:

(i) SEQUENCE CHARACTERISTICS:
        (A) LENGTH: 70 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 11
        (D) OTHER INFORMATION: /note= "Val is replaced by Asn for
            the point mutant hFas"

(xi) SEQUENCE DESCRIPTION: SEQ ID NO:5:

Gln Val Lys Gly Phe Val Arg Lys Asn Gly Val Asn Glu Ala Lys Ile
 1               5                  10                  15

Asp Glu Ile Lys Asn Asp Asn Val Gln Asp Thr Ala Glu Gln Lys Val
                20                  25                  30

Gln Leu Leu Arg Asn Trp His Gln Leu His Gly Lys Lys Glu Ala Tyr
            35                  40                  45

Asp Thr Leu Ile Lys Asp Leu Lys Lys Ala Asn Leu Cys Thr Leu Ala
            50                  55                  60

Glu Lys Ile Gln Thr Ile
 65                  70

(2) INFORMATION FOR SEQ ID NO:6:

(i) SEQUENCE CHARACTERISTICS:
        (A) LENGTH: 70 amino acids
        (B) TYPE: amino acid
```

```
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 11
            (D) OTHER INFORMATION: /note= "Leu is replaced by Asn for
                the point mutant hTNFR-1"

(xi) SEQUENCE DESCRIPTION: SEQ ID NO:6:

Arg Trp Lys Glu Phe Val Arg Arg Leu Gly Leu Ser Asp His Glu Ile
1               5                   10                  15

Asp Arg Leu Glu Leu Gln Asn Gly Arg Cys Leu Arg Glu Ala Gln Tyr
            20                  25                  30

Ser Met Leu Ala Thr Trp Arg Arg Thr Pro Arg Arg Glu Ala Thr
        35                  40                  45

Leu Glu Leu Leu Gly Arg Val Leu Arg Asp Met Asp Leu Leu Gly Cys
    50                  55                  60

Leu Glu Asp Ile Glu Glu
65                  70

(2) INFORMATION FOR SEQ ID NO:7:

(i) SEQUENCE CHARACTERISTICS:
            (A) LENGTH: 9 amino acids
            (B) TYPE: amino acid
            (C) STRANDEDNESS: single
            (D) TOPOLOGY: linear (xi) SEQUENCE DESCRIPTION: SEQ ID NO:7:

Tyr Pro Tyr Asp Val Pro Asp Tyr Ala
1               5

(2) INFORMATION FOR SEQ ID NO:8:

(i) SEQUENCE CHARACTERISTICS:
            (A) LENGTH: 6 amino acids
            (B) TYPE: amino acid
            (C) STRANDEDNESS: single
            (D) TOPOLOGY: linear (xi) SEQUENCE DESCRIPTION: SEQ ID NO:8:

Asp Thr Tyr Arg Tyr Ile
1               5

(2) INFORMATION FOR SEQ ID NO:9:

(i) SEQUENCE CHARACTERISTICS:
            (A) LENGTH: 8 amino acids
            (B) TYPE: amino acid
            (C) STRANDEDNESS: single
            (D) TOPOLOGY: linear (xi) SEQUENCE DESCRIPTION: SEQ ID NO:9:

Asp Tyr Lys Asp Asp Asp Asp Lys
1               5

(2) INFORMATION FOR SEQ ID NO:10:

(i) SEQUENCE CHARACTERISTICS:
            (A) LENGTH: 117 base pairs
            (B) TYPE: nucleic acid
            (C) STRANDEDNESS: single
            (D) TOPOLOGY: linear
```

-continued (xi) SEQUENCE DESCRIPTION: SEQ ID NO:10:

```
AAGCCTGGTA CCATGCTGGG CATCTGGACC CTCCTACCTC TGGTTCTTAC GTCTGTTGCT      60
AGATTATCGT CCAAAGACTA CAAGGACGAC GATGACAAGA GTGTTAATGC CCAAGTC        117
```

METHODS AND COMPOSITIONS FOR REGULATING FAS-ASSOCIATED APOPTOSIS

This application is a continuation of application Ser. No. 08/416,379, filed Apr. 3, 1995, now abandoned.

STATEMENT OF RIGHTS TO INVENTIONS MADE UNDER FEDERALLY SPONSORED RESEARCH

This invention was made in part during work supported by the U.S. government, including a grant from the National Institutes of Health (NIH) CA61348. The government may have certain rights in the invention.

FIELD OF THE INVENTION

This invention relates to Fas-mediated cellular functions and methods for the regulation of Fas-mediated cellular functions in a population of cells.

BACKGROUND OF THE INVENTION

Programmed cell death (PCD) is a physiologic process essential to the normal development and homeostatic maintenance of multicellular organisms (reviewed in Vaux et al. (1994) Cell 76:777–779 and Ellis et al. (1991) Ann. Rev. Cell Biol. 7:663–698). Apoptosis, often equated with PCD, refers to the morphologic alterations exhibited by "actively" dying cells which include cell shrinkage, membrane blebbing and chromatin condensation. (For a general review of apoptosis, see Tomei, L. D. and Cope, F. O. Apoptosis: The Molecular Basis of Cell Death (1991) Cold Spring Harbor Press, N.Y.; Tomei, L. D.; Cope, F. O. Apoptosis II: The Molecular Basis of Apoptosis in Disease (1994) Cold Spring Harbor Press, New York; Duvall and Wyllie (1986) Immun. Today 7(4):115–119 and Cohen (1993) Immunol. Today 14:126–130.) In contrast, necrosis, sometimes referred to as accidental cell death, is defined by the swelling and lysis of cells that are exposed to toxic stimuli.

Apoptosis has been linked to many biological processes, including embryogenesis, development of the immune system, elimination of virus-infected cells, and the maintenance of tissue homeostasis. Apoptosis also occurs as a result of human immunodeficiency virus (HIV) infection of $CD4^+$ T lymphocytes (T cells). Indeed, one of the major characteristics of AIDS is the gradual depletion of $CD4^+$ T lymphocytes during the development of the disease. Several mechanisms, including apoptosis, have been suggested to be responsible for the CD4 depletion. It is speculated that apoptotic mechanisms might be mediated either directly or by the virus replication as a consequence of the HIV envelope gene expression, or indirectly by priming uninfected cells to apoptosis when triggered by different agents.

The depletion of $CD4^+$ T cells results in the impairment of the cellular immune response. It has been reported that an inappropriate activation-induced T cell PCD causes the functional and numerical abnormalities of $T_H$ cells from HIV-infected patients, that leads to the near collapse of the patient's immune system. (Brunner, T. et al. (1995) Nature 373:441–444; Dhein, J. et al. (1995) Nature 373:438–441; and Ju, S-T. et al. (1995) Nature 373:444–448).

Therefore, it is advantageous to block apoptosis and the ensuing depletion of T cells, especially in HIV infected individuals. Accordingly, a need exists to maintain T cell function and viability in HIV infected individuals and to provide systems to screen for new drugs that may assist in maintaining the cellular immune response. This invention satisfies this need and provides related advantages as well.

SUMMARY OF THE INVENTION

This invention provides a novel purified mammalian protein designated FADD having the ability to bind the cytoplasmic region or domain of the Fas receptor.

Also provided by this invention are nucleic acid molecules that encode the mammalian protein which binds the intracellular domain of Fas.

An antibody, such as a monoclonal antibody, with specific affinity for FADD is further provided by this invention.

Methods of using the proteins, nucleic acids and antibodies described above are further provided herein.

BRIEF DESCRIPTION OF THE FIGURES

FIGS. 2A through 2D show sequence analysis of FADD and its novel death domain. FIGS. 2A through 2C (Seq. ID Nos. 1 and 2) is the cDNA sequence of FADD and the deduced amino acid sequence of the FADD protein product. The boxed nucleotides represent an in-frame stop codon 130 base pairs upstream of the initiator methionine. The 5' end of clones 8 and 15 isolated in the yeast two-hybrid screen are indicated with arrows. The death domain is underlined while the valine residue altered to an asparagine in FADDmt is indicated by the closed triangle. A potential poly (A) adenylation signal (ATTAAA) is overlined.

FIG. 2D (Seq. ID Nos. 3 through 6) shows the death domain of FADD and its amino acid sequence homology to other death domains. Solid black shading refers to identical residues and gray shading indicates conservative amino acid substitutions relative to the sequence of FADD. The arrow indicates the amino acid residue, which when substituted by an asparagine, disrupts binding and/or signaling in the respective proteins.

In FIG. 3A, a human adult tissue Northern blot (Clontech) was probed with FADD cDNA, PBL=peripheral blood leukocyte. FIG. 3B is a human fetal Northern blot (Clontech) which was probed as in FIG. 3A.

FIG. 4A is a schematic representation of the GST fusion proteins containing the cytoplasmic domains of Fas, Fas mutants, and TNFR-1. Amino acid residues are given for selected junctions and numbering is based on the mature form of the receptor. The Lpr mutant ($V^{238} \rightarrow N^{238}$) of Fas is represented by an asterisk. The gray shading represents the death domain of FAS. Binding of FADD to the various GST fusion proteins is depicted to the right.

FIG. 4B shows the interaction of in vitro translated, $^{35}$S-labeled FADD with various GST fusion proteins immobilized on glutathione-Sepharose beads. After the beads were washed, retained FADD protein was analyzed by SD5-PAGE and autoradiography (upper panel). The gel was Coomassie stained and the bands representing the various GST fusion proteins were aligned to show equivalency of loading (lower panel).

In FIG. 4C, 293T cells were transfected with HA-epitope tagged FADD (HA-FADD) and metabolically labeled with $^{35}$S-methionine and cysteine. Detergent lysates were prepared and incubated with the various GST fusion proteins immobilized on glutathione-Sepharose beads. After washing, the completed beads were dissociated and immunoprecipitated with an anti-HA (α-HA) antibody which should recognize HA-FADD. The samples were then analyzed by SDS-PAGE and autoradiography (upper panel). The respective GST fusion proteins were shown as in B (lower panel).

FIG. 5A is a schematic representation of Fas and Fas mutants transfected into 293T cells. The black square represents the FLAG-epitope tag engineered 5 amino acids downstream of the putative signal sequence of Fas. The open rounded rectangles represent the 3 cysteine-rich subdominals of the extracellular domain of Fas, while the cytoplasmic residues contain the death domain (gray rectangle) and a putative negative regulatory domain (shaded oval). Residue numbering is based on the mature form of the receptor and the amino acid sequence is given for selected junctions. The Lpr mutant ($V^{238} \rightarrow N^{238}$) of Fas is represented by an asterisk. In vivo FADD binding is described to the right of the schematic along with relative cell death caused by Fas and its mutants as described by Itoh et al. (1993) Cell 66:233–243.

Figure 5A:
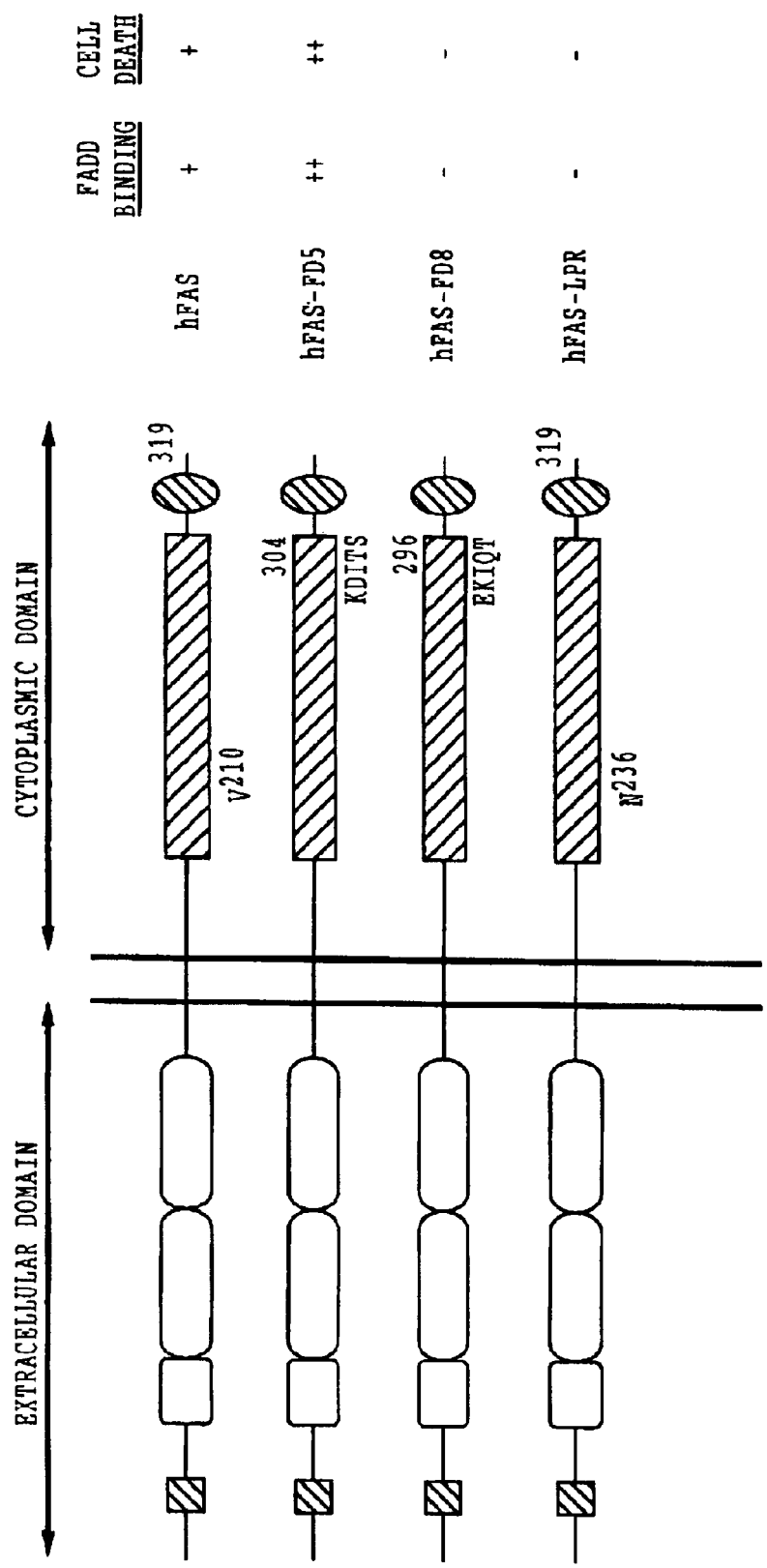
FIGS. 5A through 5C show in vivo association of FADD with Fas and Fas-FD5.
Figure 5B:
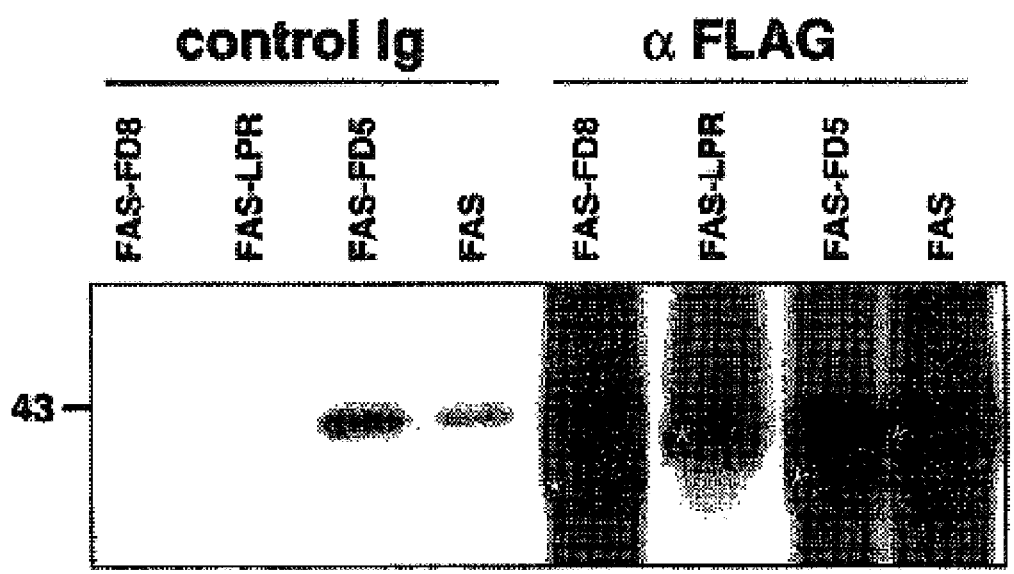

For the results shown in FIG. 5B, 293T cells were cotransfected with HA-FADD and FLAG-epitope tagged Fas and Fas mutants (as depicted in FIG. 5A) and metabolically labeled with 3S methionine and cysteine. Detergent lysates were then immunoprecipitated with anti-FLAG (α-FLAG) mAb and Isotype-matched control antibody and analyzed by SDS-PAGE and autoradiography to show expression of FLAG-tagged Fas and Fas mutants. White asterisks indicate relative position of Fas and its mutants.

Figure 5C:
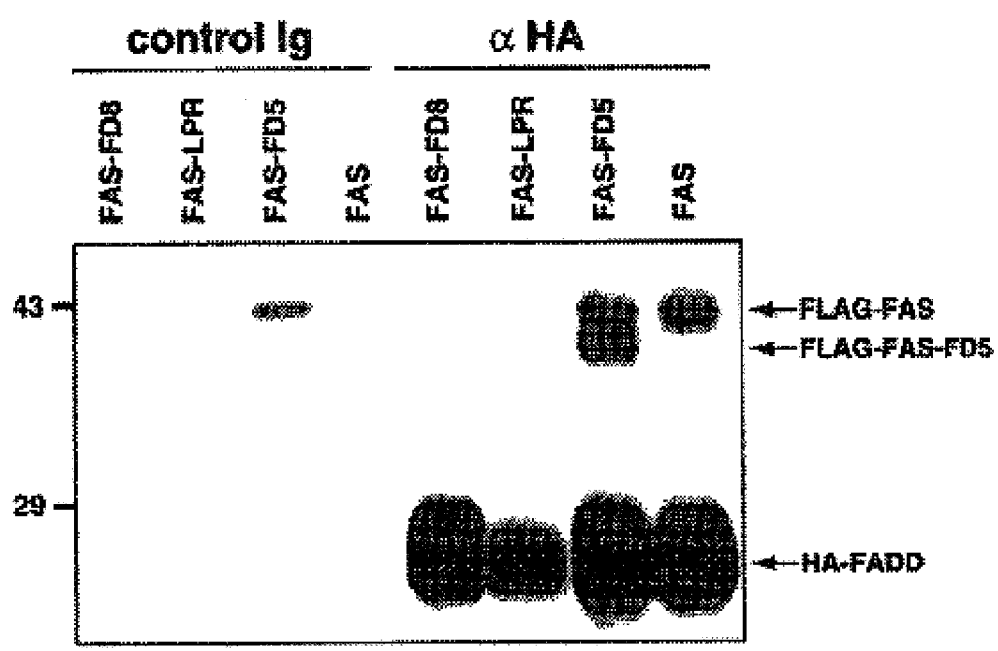

In the results shown in FIG. 5C, 293T lysates (as in FIG. 5B) also were immunoprecipitated with α-HA antibody to show HA-FADD expression.

Figure 5D:
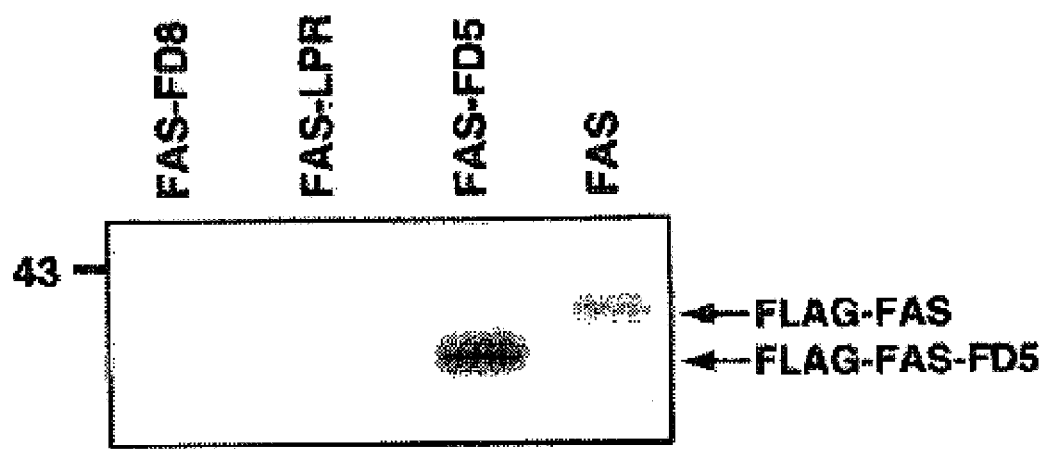

FIG. 5D shows the coimmunoprecipitation of FADD with Fas and mutants. A fraction of the α-HA immunoprecipitates (used in FIG. 5C) were dissociated and reimmunoprecipitated with an α-FLAG antibody.

Figure 6:
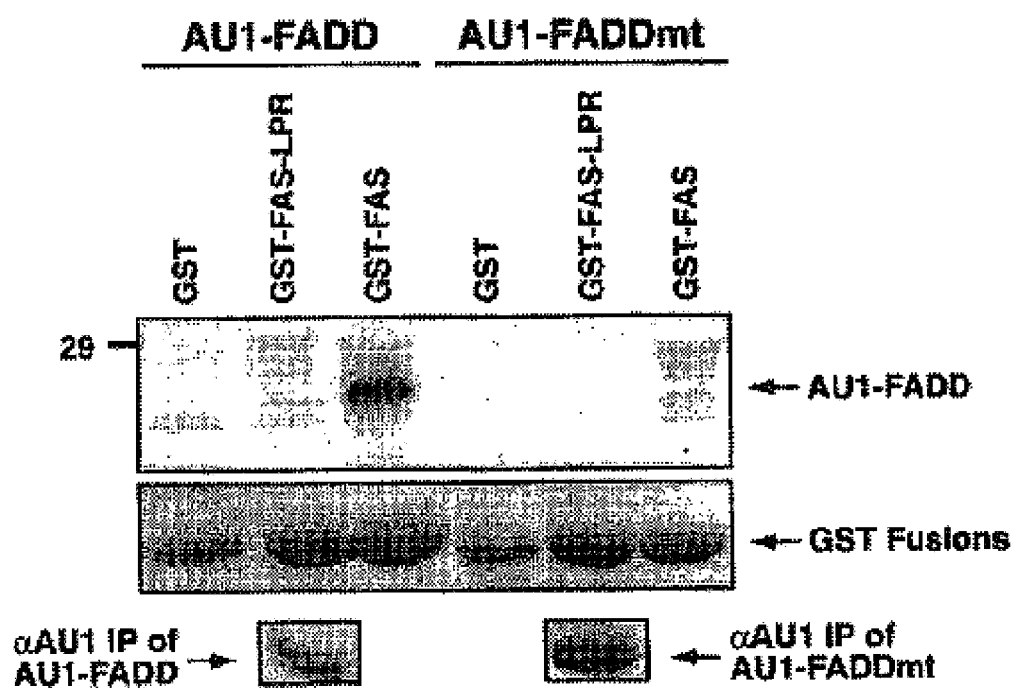

FIG. 6 shows that FADDmt fails to bind Fas, suggesting a death domain to death domain interaction. 293T cells were transfected with AU1-epitope tagged FADD (AU1-FADD) or AU1-FADDmt metabolically labeled with $^{35}$S-methionine and cysteine. Detergent lysates were prepared and incubated with various GST fusion proteins immobilized on glutathione-Sepharose beads. The samples were analyzed by SDS-PAGE and autoradiography (upper panel). The respective GST fusion proteins are shown as in FIG. 4B (middle panel). To show that equivalent amounts of AU1-FADD and AU1-FADDmt were expressed and subsequently incubated with the beads, an aliquot of the respective lysates was immunoprecipitated with α-AU1 antibody and visualized by SDS-PAGE and autoradiography (bottom panels).

Figure 7B:
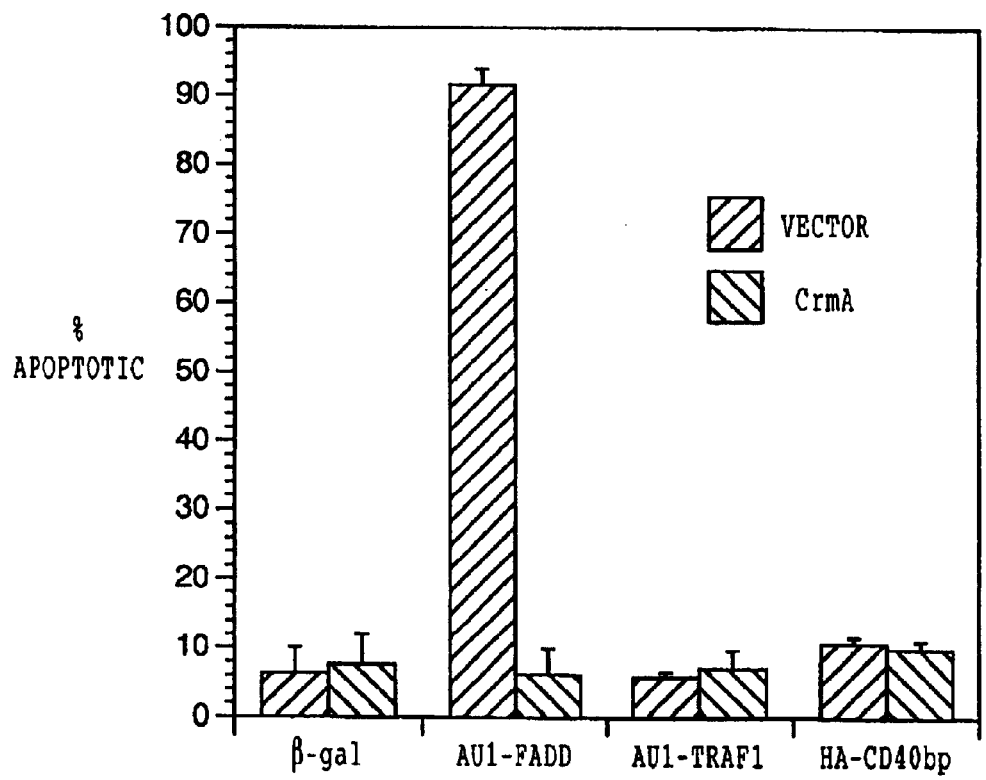
Figure 7C:
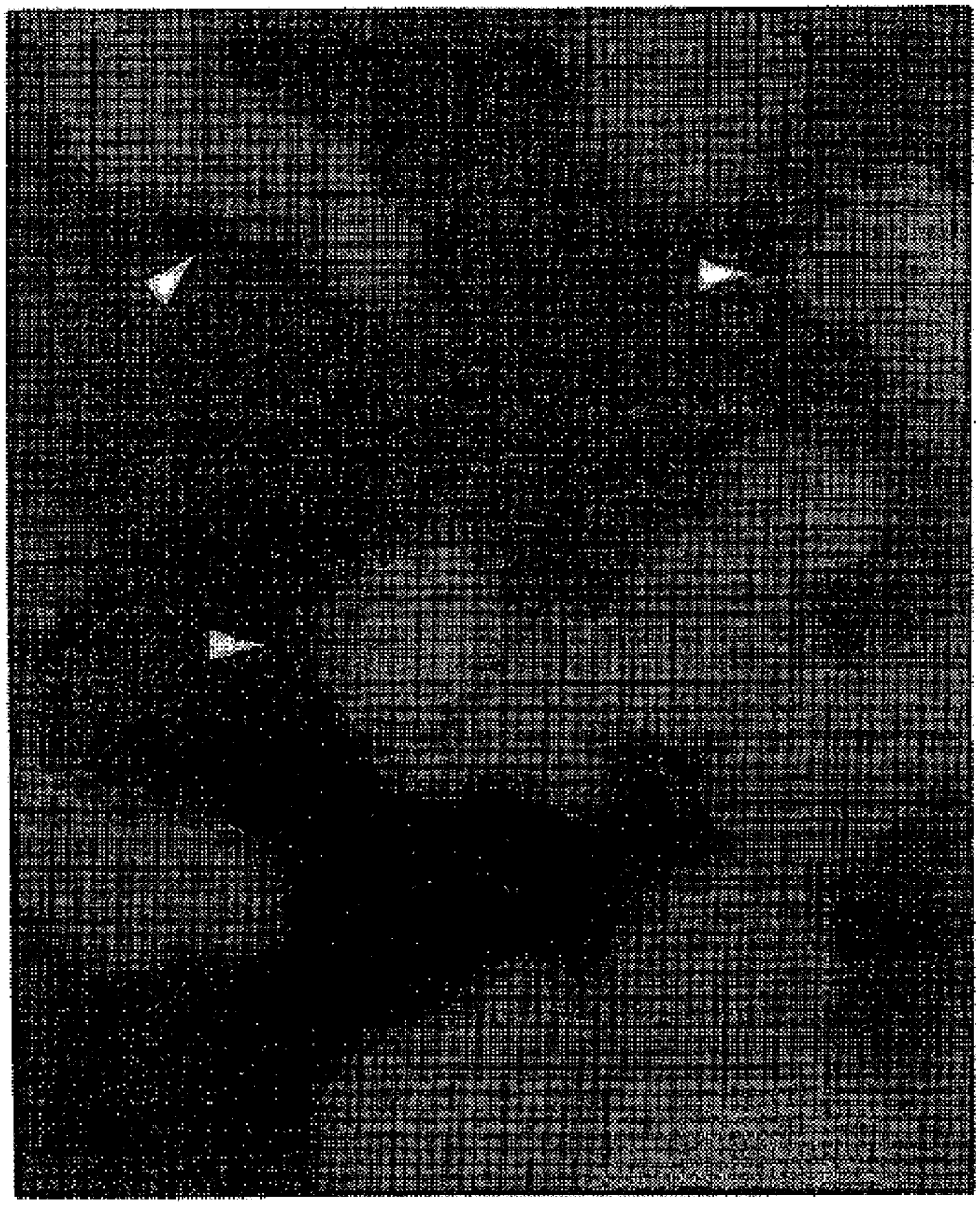

FIGS. 7A through 7C show expression of FADD in BJAB cells induces apoptosis which is inhibitable by CrmA. Shown in FIG. 7A is a previously characterized BJAB cell line expressing CrmA (as described in Tewari et al. (1995) J. Biol. Chem. 270:3255–3260) and a corresponding vector control line that were transiently transfected with pCMV β-galactosidase in the presence or absence of an equimolar quantity of pcDNA3 AU1-FADD. The cells were cytocentrifuged, fixed, and stained for β-galactosidase (yellow) and with propidium iodide (red). Vector control line transfected with β-galactosidase (Panel 1). Vector control line transfected with β-galactosidase and pcDNA3-AU1-FADD (Panel 2). CrmA-expressing line transfected with β-galactosidase (Panel 3). CrmA-expressing line transfected with β-galactosidase and pcDNA3-AU1-FADD (Panel 4).

In FIG. 7B, at least 100 transfected cells, processed as in FIG. 7A, were counted and designated as apoptotic or non-apoptotic as determined by cell morphology.

FIG. 7C shows immunostaining of AU1-FADD (green) which was transiently transfected into a BJAB cell line expressing CrmA. Propidium iodide staining (red) reveals nuclei.

Figure 8:
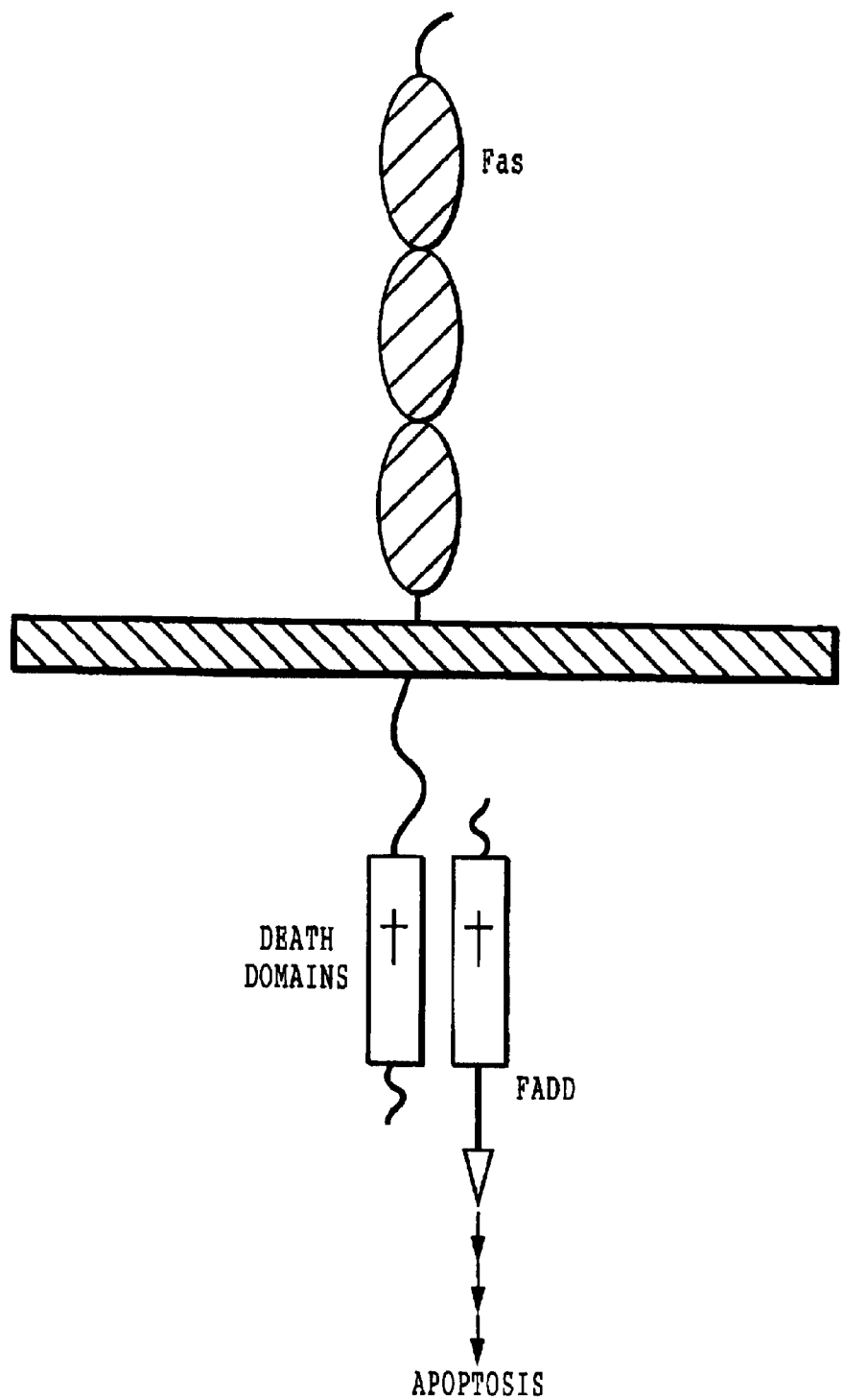

FIG. 8 is a schematic model for the interaction between FADD and Fas.

DETAILED DESCRIPTION OF THE INVENTION

Although the morphologic features of cell death are well described, the molecular mechanisms behind apoptosis remain undefined. Recent work on PCD in the nematode *Caenorhabditis elegans* suggests that CED-3 initiates the cell death program (Yuan et al. (1993) Cell 75:641–652). Sequence analysis revealed that CED-3 is similar to the mammalian interleukin-1β (IL-1β) converting enzyme (ICE); a cysteine proteinase involved in the processing and activation of pro-IL-1β to the active cytokine (Cerretti et al. (1992) Science 256:97–100 and Thornberry et al. (1992) Nature 356:768–774). Overexpression of ICE in mammalian cells induced apoptosis, suggesting that ICE, or a related protease, may be an essential component of the cell death pathway (Miura et al. (1993) Cell 75:653–660).

If a CED-3 like protease is presumed to be a distal effector of the mammalian cell death pathway, the proximal components that lead to its activation remained to be identified.

Two cell surface cytokine receptors, Fas/APO-1 antigen and the receptor for Tumor Necrosis Factor (TNF), have been shown to trigger apoptosis by natural ligands or specific agonist antibodies (Baglioni, C. (1992) The Molecules and Their Emerging Roles in Medicine (Raven Press, N.Y., N.Y.); Yonehara et al. (1989) S. J. Exp. Med. 169:1747–1756; Itoh et al. (1991) Cell 66:233–243; Trauth, B. C. et al. (1989) Science 245:301–305). The Fas antigen is involved in the negative selection of thymic T-lymphocytes and mice carrying a point mutation in the cytoplasmic domain of Fas exhibit a lupus-like lymphoproliferative autoimmune disorder (Lpr, Watanabe-Fukunaga et al. (1992) Nature 356:314–317. Recently, the Fas-mediated cell pathway has been implicated in the activation-induced death of T-cells (Dhein et al., J. (1995) supra; Brunner, T. et al. (1995); supra; and Ju et al. (1995) supra.) While the main activity of Fas is to trigger cell death, the TNF receptor (TNFR) can signal an array of diverse activities such as fibroblast proliferation, resistance to chlamidlae and synthesis of prostaglandin $E_2$ (Tartaglia, L. A. et al. (1992) Immunol. Today 13:151–153.

The activation of Fas and TNFR is caused by receptor aggregation mediated by the respective ligands or agonist antibodies. The signal is thought to be transduced by clustering of the intracellular domain (Boldin, M. P. et al. (1995) J. Biol. Chem. 270:387–391 and Song, H. Y. et al. (1994) J. Biol. Chem. 269:22492–22495) which encompasses a region which is significantly conserved in the Fas antigen as well as in TNFR-1 (Tartaglia et al. (1993) supra and Itoh, N. et al. (1993) J. Biol. Chem. 266:10932–10937). This shared "death domain" suggests that both receptors interact with a related set of signal transduction molecules that had, until this disclosure, remained unidentified.

Provided herein is the molecular cloning and characterization of "FADD" a Fas Associating protein with) a novel Death Domain. The specific interaction of Fas and FADD is due to the association of their respective homologous death domains. Remarkably similar to Fas-induced killing, overexpression of FADD induces apoptosis which is inhibitable by CrmA. Accordingly, FADD is a component of the Fas-receptor mediated pathway and particularly Fas-induced apoptosis.

Proteins and Polypeptides

This invention provides purified proteins having the ability to bind the cytoplasmic region of the Fas receptor. In one embodiment, the purified proteins of this invention, termed "FADD proteins" are defined by their specific ability to bind to the cytoplasmic domain of the Fas receptor and Fas-FD5, a mutant of Fas possessing enhanced killing activity, but not the functionally inactive mutants Fas-LPR and Fas-FD8.

In one embodiment of this invention, a purified protein is a 208 amino acid human protein having an apparent molecular weight of about 22 to 24 kDa and more particularly about 23.3 kDa, as determined by an SDS polyacrylamide gel under reducing conditions. In a separate embodiment, a protein has the amino acid sequence shown in FIGS. 2A through 2C and Sequence ID. No. 2). Also provided by this invention are polypeptide fragments of the mammalian protein, the human 23.3 kD protein or the protein having the amino acid sequence shown in FIGS. 2A through 2C, each defined by the ability to bind to the cytoplasmic domain of the Fas receptor using, for example, the in vitro binding assay described below. These polypeptide fragments can include any fragment containing from about amino acid 41 to amino acid 208 or the C-terminal half of FADD as depicted in FIGS. 2A through 2C.

It is understood that functional equivalents of the protein also shown in FIGS. 2A through 2C, the 23.3 kD purified protein, or the polypeptide fragments thereof, e.g., as shown in FIGS. 2A through 2C, and equivalents thereof, also are within the scope of this invention. One such equivalent includes chemical structures other than amino acids which functionally mimic the binding of FADD to the cytoplasmic domain of the Fas receptor ("muteins"). An additional example of an equivalent is a protein or polypeptide containing a distinct protein or polypeptide joined to FADD or its equivalent which varies the primary sequence of protein of this invention from the sequences provided in FIGS. 2A through 2C without necessarily affecting the binding of the resultant polypeptide or protein to the cytoplasmic domain of Fas. Where specific amino acids or other structures or sequences beyond the sequence shown in FIGS. 2A through 2C are presented, it is intended that various modifications which do not destroy the function of the binding site are within the definition of the proteins encompassed by this invention. For the purposes of this invention, the term "FADD protein" is intended to mean all of the proteins, polypeptides, fragments and equivalents thereof, having the ability to bind the cytoplasmic domain of Fas.

An agent having the ability to inhibit the ability of FADD to bind to the cytoplasmic domain of the Fas receptor is further provided by this invention. Such agents include, but are not limited to, an anti-FADD antibody, a dominant inhibitory fragment of FADD or a soluble intracellular Fas. "Soluble intracellular Fas" is an intracellular portion of the Fas receptor which binds FADD.

The terms "proteins" and "polypeptides" also are intended to include molecules containing amino acids linearly coupled through peptide bonds. As used herein, the term "peptide bond" or "peptide linkage" refers to an amide linkage between a carboxyl group of one amino acid and the α-amino group of another amino acid. Such polypeptides also can contain amino acid derivatives or non-amino acid moieties. The amino acids can be in the L or D form so long as the binding function of the polypeptide is maintained. The term amino acid refers both to the naturally occurring amino acids and their derivatives, such as TyrMe and PheCl, as well as other moieties characterized by the presence of both an available carboxyl group and an amine group. Non-amino acid moieties which can be contained in such polypeptides include, for example, amino acid mimicking structures. Mimicking structures are those structures which exhibit substantially the same spatial arrangement of functional groups as amino acids but do not necessarily have both the α-amino and α-carboxyl groups characteristic of amino acids.

As used herein, the term "hydrophobic" is intended to include those amino acids, amino acid derivatives, amino acid mimics and chemical moieties which are non-polar. Hydrophobic amino acids include Phe, Val, Trp, Ile and Leu. As used herein, the term "positively charged amino acid" refers to those amino acids, amino acid derivatives, amino acid mimics and chemical moieties which are positively charged. Positively charged amino acids include, for example, Lys, Arg and His.

The proteins and polypeptides of this invention are distinct from native or naturally occurring proteins or polypeptides because they exist in a purified state. As used herein, the term "purified" when referring to a protein or a polypeptide or any of the intended variations as described herein shall mean that the compound or molecule is substantially free of contaminants normally associated with a native or natural environment.

The proteins and polypeptides of this invention can be obtained by a number of methods well known to those of skill in the art, which include purification, chemical synthesis and recombinant methods. For example, the proteins and polypeptides can be purified from a $Fas_+$ cell or tissue lysates using methods such as immuno-precipitation with anti-FADD antibody, and standard techniques such as gel filtration, ion-exchange, reversed-phase, and affinity chromatography using a FADD fusion protein as shown herein. For such methodology, see for example Deutscher et al., *Guide to Protein Purification: Methods in Enzymology* (1990) Vol. 182, Academic Press.

The proteins and polypeptides also can be obtained by chemical synthesis using a commercially available automated peptide synthesizer such as those manufactured by Applied Biosystems, Inc., Model 430A or 431A, Foster City, Calif. and the amino acid sequence provided in FIGS. 2A through 2C. The material so synthesized can be precipitated and further purified, for example by high performance liquid chromatography (HPLC).

Alternatively, the proteins and polypeptides can be obtained by well-known recombinant methods as described, for example, in Sambrook et al., *Molecular Cloning: A Laboratory Manual* 2d ed. (Cold Spring Harbor Laboratory (1989)) using the host vector systems described and exemplified below.

The FADD protein and polypeptides have several utilities. For example, they can be bound to a column and used for the purification of Fas receptors. They also are useful as immunogens for the production of anti-FADD antibodies as described below. They have further utility in an in vitro assay system to screen for agents or drugs which either inhibit or augment the FADD/Fas-receptor pathway and to test possible therapies.

When used to detect Fas or to screen for new Fas-regulating agents, FADD can be bound to a solid phase carrier for example, glass, polystyrene, polyethylene, dextran, nylon, natural and modified celluloses, polyacrylamides, glutathione-agarose beads and agaroses. Those skilled in the art will know of other suitable carriers for this purpose. Accordingly, this invention also provides a method of detecting Fas in a cell sample by first immobilizing FADD onto a solid support such as glutathione-agarose beads at a suitable concentration, eg., between about 5 mg/ml to about 12 mg/ml, and more preferably between about 6 mg/ml and about 10 mg/ml. The sample containing or suspected of containing Fas is prepared and contacted with the beads under conditions favoring binding between the Fas receptor and FADD. Suitable conditions are for example, those set forth in the experiment section described below. The beads are then subjected to conditions to release the complex from the solid support and protein complex can then be visualized by autoradiography.

The proteins of this invention also can be combined with various liquid phase carriers, such as sterile or aqueous solutions, pharmaceutically acceptable carriers as defined below, suspensions and emulsions. Examples of non-aqueous solvents include propyl ethylene glycol, polyethylene glycol and vegetable oils. When used to prepare antibodies, the carriers also can include an adjuvant which is useful to non-specifically augment a specific immune response. A skilled artisan can easily determine whether an adjuvant is required and select one. However, for the purpose of illustration only, suitable adjuvants include, but are not limited to Freund's Complete and Incomplete, mineral salts and polynucleotides.

Nucleic Acids

Isolated nucleic acid molecules which encode amino acid sequences corresponding to FADD protein, mutein, antibodies and active fragments thereof are further provided by this invention. As used herein, "nucleic acid" shall mean single and double stranded DNA, cDNA and RNA, including anti-sense RNA. One can obtain an anti-sense RNA using the sequence provided in FIGS. 2A through 2C and the methodology described in Vander Krol et al. (1988) *BioTechniques* 6:958. "Isolated" means separated from other cellular components normally associated with DNA or RNA intracellularly.

In one aspect of this invention, the nucleic acid molecule encoding FADD protein or polypeptide has the sequence or parts thereof shown in FIGS. 2A through 2C.

The invention also encompasses nucleic acid molecules which differ from that of the nucleic acid molecules shown in FIGS. 2A through 2C, but which produce the same phenotypic effect. These altered, but phenotypically equivalent nucleic acid molecules are referred to "equivalent nucleic acids." Examples of such "equivalent nucleic acids" are those molecules which have a sequence which is homologous to sequence of in FIGS. 2A through 2C, and preferably have a homology of greater than about 50%, more preferably in excess of 90%. A homology of about 99% is most preferred. This invention also encompasses nucleic acid molecules characterized by changes in non-coding regions that do not alter the phenotype of the polypeptide produced therefrom when compared to the nucleic acid molecule described hereinabove. This invention further encompasses nucleic acid molecules which hybridize to the nucleic acid molecule of the subject invention.

The nucleic acid molecules of this invention can be isolated using the technique described in the experimental section described below or replicated using PCR (Perkin-Elmer) and the methods described below. For example, the sequence can be chemically replicated using PCR (Perkin-Elmer) which in combination with the synthesis of oligonucleotides, allows easy reproduction of DNA sequences. The PCR technology is the subject matter of U.S. Pat. Nos. 4,683,195, 4,800,159, 4,754,065, and 4,683,202. Alternatively, one of skill in the art can use the sequence provided herein and a commercial DNA synthesizer to replicate the DNA. RNA can be obtained by using the isolated DNA and inserting it into a suitable cell where it is transcribed into RNA. The RNA can then be isolated using methods well known to those of skill in the art, for example, as set forth in Sambrook et al. (1989) supra.

The invention further provides the isolated nucleic acid molecule operatively linked to a promoter of RNA transcription, as well as other regulatory sequences for replication and/or expression of the DNA or RNA. As used herein, the term "operatively linked" means positioned in such a manner that the promoter will direct the transcription of RNA off the nucleic acid molecule. Examples of such promoters are SP6, T4 and T7. Vectors which contain a promoter or a promoter/enhancer, with termination codons and selectable marker sequences, as well as a cloning site into which an inserted piece of DNA can be operatively linked to that promoter are well known in the art. See for example, Gacesa and Ramji, *Vectors: Essential Data Series* (1994) John Wiley & Sons, N.Y., which contains maps, functional properties, commercial suppliers and a reference to GenEMBL accession numbers for various suitable vectors. Preferable, these vectors are capable of transcribing RNA in vitro or in vivo.

Fragments of the sequence shown in FIGS. 2A through 2C, e.g., a fragment comprising nucleic acids coding for amino acid residues 111–170 as shown in FIGS. 2A through 2C, and its equivalents are useful as probes to identify transcripts of the protein which may or may not be present. The fragments also may be used as PCR primers. These nucleic acid fragments can by prepared, for example, by restriction enzyme digestion of the nucleic acid molecule of FIGS. 2A through 2C and then labeled with a detectable marker such as a radioisotope using well known methods. Alternatively, random fragments can be generated using nick translation of the molecule. For methodology for the preparation and labeling of such fragments, see Sambrook et al., *Molecular Cloning: A Laboratory Manual* Cold Spring Harbor Press, Cold Spring Harbor, N.Y. (1989) supra. Nucleic acid fragments of at least 10 nucleotides are useful as hybridization probes primers. Isolated nucleic acid fragments also are useful to generate novel peptides. These peptides, in turn, are useful as immunogens for the generation of polyclonal and monoclonal antibodies.

As noted above, an isolated nucleic acid molecule of this invention can be operatively linked to a promoter of RNA transcription. These nucleic acid molecules are useful for the recombinant production of FADD and anti-FADD proteins and polypeptides or as vectors for use in gene therapy. Accordingly, this invention also provides a vector having inserted therein an isolated nucleic acid molecule described above, for example, a viral vector, such as bacteriophages, baculoviruses and retroviruses, or cosmids, plasmids and other recombination vectors. Nucleic acid molecules are inserted into vector genomes by methods well known in the art. For example, insert and vector DNA can both be exposed to a restriction enzyme to create complementary ends on both molecules that base pair with each other and which are then joined together with a ligase. Alternatively, synthetic nucleic acid linkers can be ligated to the insert DNA that correspond to a restriction site in the vector DNA, which is then digested with a restriction enzyme that recognizes a particular nucleotide sequence. Additionally, an oligonucleotide containing a termination codon and an appropriate restriction site can be ligated for insertion into a vector containing, for example, some or all of the following: a selectable marker gene, such as neomycin gene for selection of stable or transient transfectants in mammalian cells; enhancer/promoter sequences from the immediate early gene of human cytomegalovirus (CMV) for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and anti-sense RNA.

An additional example of a vector construct of this invention is a bacterial expression vector including a promoter such as the lac promoter and for transcription initiation, the Shine-Dalgarno sequence and the start codon AUG (Sambrook et al., (1989) supra). Similarly, a eucaryotic expression vector is a heterologous or homologous promoter for RNA polymerase II, a downstream polyadenylation signal, the start codon AUG, and a termination codon for detachment of the ribosome. Such vectors can be obtained commercially or assembled by the sequences described in methods noted above.

Expression vectors containing these nucleic acids are useful to obtain host vector systems to produce FADD and anti-FADD proteins and polypeptides. It is implied that these expression vectors must be replicable in the host organisms either as episomes or as an integral part of the chromosomal DNA. Suitable expression vectors include viral vectors, including adenoviruses, adeno-associated viruses, retroviruses, cosmids, etc. Adenoviral vectors are particularly useful for introducing genes into tissues in vivo because of their high levels of expression and efficient transformation of cells both in vitro and in vivo. When a nucleic acid is inserted into a suitable host cell, e.g., a procaryotic or a eucaryotic cell and the host cell replicates, the protein can be recombinantly produced. Suitable host cells will depend on the vector and can include mammalian cells, animal cells, human cells, simian cells, insect cells, yeast cells, and bacterial cells constructed using well known methods. See Sambrook et al., (1989) supra. In addition to the use of viral vector for insertion of exogenous nucleic acid into cells, the nucleic acid can be inserted into the host cell by methods well known in the art such as transformation for bacterial cells; transfection using calcium phosphate precipitation for mammalian cells; or DEAE-dextran; electroporation; or microinjection. See Sambrook et al. (1989) supra for this methodology. Thus, this invention also provides a host cell, e.g. a mammalian cell, a animal cell, a human cell, or a bacterial cell, containing a nucleic acid molecule encoding a FADD or anti-FADD protein or polypeptide.

Using the host vector system described above, a method of producing recombinant FADD or anti-FADD or active fragments thereof is provided by growing the host cells described herein under suitable conditions such that the nucleic acid encoding the FADD or anti-FADD protein or polypeptide is expressed. Suitable conditions can be determined using methods well known to those of skill in the art, see for example, Sambrook et al., (1989) supra. Proteins and polypeptides purified from the cellular extract and thereby produced in this manner also are provided by this invention.

A vector containing the isolated nucleic acid encoding FADD or anti-FADD protein also is useful for gene therapy to modulate Fas-induced or to modulate or regulate cellular functions such as apoptosis and immune disorders mediated by the Fas pathway. The terms "Fas$^+$ cellular function" is intended to mean cellular functions which are affected by the binding of the receptor to its extracellular ligands, i.e., alone or in combination with each other. In some instances, it is desireable to augment Fas$^+$ function to induce apoptosis by introducing into the cell FADD protein or FADD nucleic acid. In other instances, it is desirable to down-regulate Fas$^+$ cellular function by introducing into the cell a anti-FADD antibody or a nucleic acid encoding an anti-FADD antibody or alternatively, a FADD fragment or nucleic acid encoding it which is a dominant negative inhibitor of functionally intact native FADD. This therapy will inhibit or disable intracellular Fas signaling and therefore is a useful therapy where apoptotic cell death is to be avoided, such as in an HIV-infected T cell.

When used for gene therapy, a pharmaceutically acceptable vector is preferred, such as a replication-incompetent retroviral vector. As used herein, the term "pharmaceutically acceptable vector" includes, but is not limited to, a vector or delivery vehicle having the ability to selectively target and introduce the nucleic acid into dividing cells. An example of such a vector is a "replication-incompetent" vector defined by its inability to produce viral proteins, precluding spread of the vector in the infected host cell. An example of a replication-incompetent retroviral vector is LNL6 (Miller, A. D. et al., (1989) *BioTechniques* 7:980–990). The methodology of using replication-incompetent retroviruses for retroviral-mediated gene transfer of gene markers is well established (Correll, et al. (1989), *PNAS USA* 86:8912; Bordignon, (1989), *PNAS USA* 86:8912–52; Culver, K., (1991), *PNAS USA* 88:3155; and Rill, D. R. (1991), *Blood* 79(10):2694–700. Clinical investigations have shown that there are few or no adverse effects associated with the viral vectors, see Anderson, (1992), *Science* 256:808–13.

Antibodies

Also provided by this invention is an antibody capable of specifically forming a complex with FADD protein or a fragment thereof, as well as nucleic acids encoding them. Vectors and host cells containing these nucleic acids also are encompassed by this invention. The term "antibody" includes polyclonal antibodies and monoclonal antibodies. The antibodies include, but are not limited to mouse, rat, rabbit or human antibodies.

As used herein, an "antibody or polyclonal antibody" means a protein that is produced in response to immunization with an antigen or receptor. The term "monoclonal antibody" means an immunoglobulin derived from a single clone of cells. All monoclonal antibodies derived from the clone are chemically and structurally identical, and specific for a single antigenic determinant. The hybridoma cell lines producing the monoclonal antibodies also are within the scope of this invention.

Laboratory methods for producing polyclonal antibodies and monoclonal antibodies, as well as deducing their corresponding nucleic acid sequences, are known in the art, see Harlow and Lane, *Antibodies: A Laboratory Manual*, Cold Spring Harbor Laboratory, N.Y. (1988) and Sambrook et al. (1989) supra. The monoclonal antibodies of this invention can be biologically produced by introducing FADD or a fragment thereof into an animal, e.g., a mouse or a rabbit. The antibody producing cells in the animal are isolated and fused with myeloma cells or heteromyeloma cells to produce hybrid cells or hybridomas. Accordingly, the hybridoma cells producing the monoclonal antibodies of this invention also are provided.

Thus, using the FADD protein or fragment thereof, and well known methods, one of skill in the art can produce and screen the hybridoma cells and antibodies of this invention for antibodies having the ability to bind FADD.

If a monoclonal antibody being tested binds with FADD protein, then the antibody being tested and the antibodies provided by the hybridomas of this invention are equivalent. It also is possible to determine without undue experimentation, whether an antibody has the same specificity as the monoclonal antibody of this invention by determining whether the antibody being tested prevents a monoclonal antibody of this invention from binding FADD with which the monoclonal antibody is normally reactive. If the antibody being tested competes with the monoclonal antibody of the invention as shown by a decrease in binding by the monoclonal antibody of this invention, then it is likely that the two antibodies bind to the same or a closely related epitope. Alternatively, one can pre-incubate the monoclonal antibody of this invention with FADD protein with which it is normally reactive, and determine if the monoclonal antibody being tested is inhibited in its ability to bind the antigen. If the monoclonal antibody being tested is inhibited then, in all likelihood, it has the same, or a closely related, epitopic specificity as the monoclonal antibody of this invention.

The term "antibody" also is intended to include antibodies of all isotypes. Particular isotypes of a monoclonal antibody can be prepared either directly by selecting from the initial fusion, or prepared secondarily, from a parental hybridoma secreting a monoclonal antibody of different isotype by using the sib selection technique to isolate class switch variants using the procedure described in Steplewski et al. (1985) *Proc. Natl. Acad. Sci.* 82:8653 or Spira et al. (1984) *J. Immunol. Methods* 74:307.

This invention also provides biological active fragments of the polyclonal and monoclonal antibodies described above. These "antibody fragments" retain some ability to selectively bind with its antigen or immunogen. Such antibody fragments can include, but are not limited to:

(1) Fab, the fragment which contains a monovalent antigen-binding fragment of an antibody molecule produced by digestion with the enzyme papain to yield an intact light chain and a portion of one heavy chain;

(2) Fab', the fragment of an antibody molecule obtained by treating with pepsin, followed by reduction, to yield an intact light chain and a portion of the heavy chain; two Fab' fragments are obtained per antibody molecule;

(3) (Fab')$_2$, the fragment of the antibody that is obtained by treating with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) SCA, defined as a genetically engineered molecule containing the variable region of the light chain, the variable region of the heavy chain, linked by a suitable polypeptide linker as a genetically fused single chain molecule.

A specific examples of "biologically active antibody fragment" include the CDR regions of the antibodies. Methods of making these fragments are known in the art, see for example, Harlow and Lane, (1988) supra.

The antibodies of this invention also can be modified to create chimeric antibodies (Oi, et al. (1986) *BioTechniques* 4(3):214). Chimeric antibodies are those in which the various domains of the antibodies' heavy and light chains are coded for by DNA from more than one species.

The isolation of other hybridomas secreting monoclonal antibodies with the specificity of the monoclonal antibodies of the invention can also be accomplished by one of ordinary skill in the art by producing anti-idiotypic antibodies (Herlyn, et al., *Science*, 232:100, 1986). An anti-idiotypic antibody is an antibody which recognizes unique determinants present on the monoclonal antibody produced by the hybridoma of interest. These determinants are located in the hypervariable region of the antibody. It is this region which binds to a given epitope and, thus, it is responsible for the specificity of the antibody. The anti-idiotypic antibody can be prepared by immunizing an animal with the monoclonal antibody of interest. The animal immunized will recognize and respond to the idiotypic determinants of the immunizing antibody by producing an antibody,to these idiotypic determinants. By using the anti-idiotypic antibodies of the second animal, which are specific for the monoclonal antibodies produced by a single hybridoma which was used to immunize the second animal, it is now possible to identify other clones with the same idiotype as the antibody of the hybridoma used for immunization.

Idiotypic identity between monoclonal antibodies of two hybridomas demonstrates that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the mirror image of the epitope bound by the first monoclonal antibody. Thus, in this instance, the anti-idiotypic monoclonal antibody could be used for immunization for production of these antibodies.

As used in this invention, the term "epitope" is meant to include any determinant having specific affinity for the monoclonal antibodies of the invention. Epitopic determinants usually consist of chemically active surface groupings of molecules such as amino acids or sugar side chains and usually have specific three dimensional structural characteristics, as well as specific charge characteristics.

Also encompassed by this invention are proteins or polypeptides that have been recombinantly produced, biochemically synthesized, chemically synthesized or chemically modified, that retain the ability to bind FADD, the intracellular binding domain of the Fas receptor, or a fragment thereof, as the corresponding native polyclonal or monoclonal antibody.

The antibodies of this invention can be linked to a detectable agent or a hapten. The complex is useful to detect the Fas receptor or FADD protein or fragments in a sample or detect agents which interfere with FADD-Fas receptor binding, using standard immunochemical techniques such as immunohistochemistry as described by Harlow and Lane (1988) supra. Examples of types of immunoassays which can utilize monoclonal antibodies of the invention are competitive and non-competitive immunoassays in either a direct or indirect format. Examples of such immunoassays are the enzyme linked immunoassay (ELISA) radioimmunoassay (RIA) and the sandwich (immunometric) assay.

Detection of using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

Another technique which may also result in greater sensitivity consists of coupling the antibodies to low molecular weight haptens. These haptens can then be specifically detected by means of a second reaction. For example, it is common to use such haptens as biotin, which reacts avidin, or dinitropherryl, pyridoxal, and fluorescein, which can react with specific anti-hapten antibodies. See Harlow and Lane (1988) supra.

The monoclonal antibodies of the invention can be bound to many different carriers. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibody, or will be able to ascertain such, using routine experimentation. Furthermore, the binding of these labels to the monoclonal antibody of the invention can be done using standard techniques common to those of ordinary skill in the art.

For purposes of the invention, FADD may be detected by the monoclonal antibodies of the invention when present in biological fluids and tissues. Any sample of $Fas^{30}$ cell or tissue lysate containing a detectable amount of FADD can be used.

Compositions

This invention also provides compositions containing any of the above-mentioned proteins, muteins, polypeptides or fragments thereof, and an acceptable solid or liquid carrier. When the compositions are used pharmaceutically, they are combined with a "pharmaceutically acceptable carrier" for administration. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, *Remington's Pharm. Sci.*, 15th Ed. (Mack Publ. Co., Easton (1975)). These compositions can be used for the preparation of medicaments for the diagnosis and treatment of pathologies associated with the loss of the Fas receptor pathway.

Utilities

The use of the compositions and methods in vitro provides a powerful bioassay for screening for drugs which are agonists or antagonists of Fas-FADD pathway in $Fas^+$ cells. A $Fas^+$ cell is one which contains the Fas receptor or which is induced to PCD by an endogenous agent such as HIV, anti-TCR antibody, TNF and anti-Fas antibody. In one embodiment, these cells constitutively and inducibly express receptors for either or both of the cytokine tumor necrosis factor (TNF) or the cell death transducing receptor Fas or TCR and which have been activated by their respective ligand. Recently, three separate groups have reported that Fas-induced apoptosis is involved in T cell death. Specifically, one group has shown that the Fas receptor, which can transduce a potent apoptotic signal when ligated, is rapidly expressed following activation on T cell hybridomas. It was suggested that the Fas receptor-ligand interaction induces cell death in a cell-autonomous manner. See Dhein et al. (1995) *Nature* 373:438–441; Brunner et al. (1995)*Nature* 373:441–444; and Ju et al. (1995) *Nature* 373:444–448.

For the purpose of illustration only, examples of suitable cells are T lymphocytes (T cells) (e.g., $TCR^+$, $CD4^+$ and $CD8^+$ T cells) leukocytes and mixed leukocyte cultures (MLC), B lymphoma cells (e.g., A202J (ATCC)), bone marrow cells, endothelial cells, breast carcinoma cells, fibroblast cells, epithelial tumor cells (see Spriggs, D. R. et al. (1988) *J. Clin. Inves.* 81:455–460) and monocytes. Because Fas (APO-1/CD95) cell surface is a member of the nerve growth factor (NGF)/tumor necrosis factor (TNF) receptor superfamily, any cell having a receptor of this family is intended to be encompassed by the scope of this invention. Fas and TNF receptor expression also has been identified on numerous tissues, see for example Watanabe-Fukunaga et al. (1992) *J. Immun.* 148:1049–1054 and Owen-Schaub, L. B. et al. (1994) *Cancer Res.* 54:1580–1586; Dhein et al. (1995) *Nature* 373:438–441; Brunner et al. (1995) *Nature* 373:441–444; and Ju et al. (1995) *Nature* 373:444–448. Assays for identifying additional "suitable" cells sensitive to induction or activation, e.g., TCR-, TNF- or Fas-related apoptosis, are well known to those of skill in the art. (See for example, Opipairi, et al. *J. Biol. Chem.* (1992) 267:12424–12427; Yonehara et al. *J. Exp. Med.* (1989) 169:1747–1756; Dhein et al. (1995) supra; Brunner et al. (1995) supra and Ju et al. (1995) supra) However, this method is particularly suitable for use with $TCR^+$, $CD8^+$ or $CD4^+$ T cells or tissues that harbor the simian immunodeficiency virus (SIV) or alternatively, the human immunodeficiency virus (HIV). The cells can be mammalian cells or animal cells, such as guinea pig cells, rabbit cells, simian cells, mouse cells, rat cells, or human cells. They can be continuously cultured or isolated from an animal or human. In a separate embodiment of this invention, neurological cells are specifically excluded.

It also provides a powerful assay to determine whether an agent of interest, such as a pharmaceutical, is useful to treat a Fas-mediated disorder or to further augment or disable Fas receptor function. For example, the composition to be tested can be added prior to, simultaneously or subsequent to FADD as described above. A separate "control" assay is run simultaneously under the same conditions but without the addition of the composition or drug being tested. If the agent inhibits binding of FADD to the intracellular Fas domain (as compared to control) the agent is a candidate for inhibiting or preventing Fas receptor mediated function in the cell, tissue or subject.

More specifically, the in vitro method comprises providing cell cultures or tissue cultures having either a cell surface receptor that mediates apoptosis such as a TCR, the TNF receptor or the Fas receptor. The cells are cultured under conditions (temperature, growth or culture medium and gas ($CO_2$)) and for an appropriate amount of time to attain exponential proliferation without density dependent constraints. The cells are then exposed to preliminary conditions necessary for apoptosis, for example an effective amount of an inducing agent, e.g., a TCR ligand, HIV, SIV, TNF, or a Fas ligand such as an anti-Fas antibody is added to the culture. Anti-Fas antibodies and mitogens (ConA) are well known to those of skill in the art. (Itoh, N. et al. (1991) *Cell* 66:233–243 and Yonehara et al. (1989) *J. Exp. Med.* (1989) 169:1747–1756). These cells are now "induced" to apoptosis. The cells are again cultured under suitable temperature and time conditions. In one embodiment, HIV or SIV is added to the culture. In other embodiments, a drug or agent to be tested is added in varying concentrations at a time that is simultaneous with, prior to, or after the inducing agent.

The FADD nucleic acid or protein is then added to the culture in an effective amount and the cells are cultured under suitable temperature and time conditions to induce apoptosis. The FADD nucleic acid or protein can be added prior to, simultaneously with, or after, the inducing agent. The cells are assayed for apoptotic activity using methods well known to those of skill in the art and described herein. It is apparent to those of skill in the art that two separate culture of cells must be treated and maintained as the test population. One is maintained without receiving an inducing agent to determine background release and the second without receiving the agent to be tested. The second population of cells acts as a control.

The use of the compositions and methods in vitro provides a powerful bioassay for screening for drugs which are agonists or antagonists of Fas mediated cellular function in these cells. Thus, one can screen for drugs having similar or enhanced ability to prevent or inhibit apoptosis. The in vitro method further provides an assay to determine if the method of this invention is useful to treat a subject's pathological condition or disease that has been linked to apoptotic cell death in the individual.

When the method is practiced in vivo in a human patient, it is unnecessary to provide the inducing agent since it is provided by the patient's immune system. However, when practiced in an experimental animal model, it can be necessary to provide an effective amount of the inducing agent in a pharmaceutically acceptable carrier prior to administration of the FADD or anti-FADD product, to induce apoptosis. When the method is practiced in vivo, the carrying vector, polypeptide, polypeptide equivalent, or expression vector can be added to a pharmaceutically acceptable carrier and systemically administered to the subject, such as a human patient or an animal such as a mouse, a guinea pig, a simian, a rabbit or a rat. Alternatively, it can be directly infused into the cell by microinjection. A fusion protein also can be constructed comprising the T-cell specific ligand for targeting to a T cell. Such T cell specific ligands include, but are not limited to anti-CD3, anti-CD4, anti-CD28 and anti-IL-1 antibody protein.

Accordingly, this invention also provides a method for screening for an agent to regulate the Fas receptor pathway, comprising the steps of: a) providing a Fas cytoplasmic domain receptor bound to a solid support; b) contacting the agent to be tested with the receptor bound support of step a) under conditions favoring binding of the cytoplasmic domain to the receptor to FADD; c) contacting detectably-labeled FADD to the solid support of step b) under conditions favoring binding of Fas cytoplasmic domain receptor to FADD; d) detecting the presence of any complex formed between the Fas receptor and FADD to form Fas receptor-FADD complex; and e) the absence of complex being indicative that the agent inhibits binding of FADD to the Fas receptor and therefore is an agent to inhibit Fas mediated function such as apoptosis.

This invention provides an alternative method for screening for a FADD or Fas-receptor immunosuppressive agent, which comprises the steps of a) providing a Fas cytoplasmic domain receptor bound to a solid support; b) contacting detectably-labeled FADD to the solid support of step a) under conditions favoring binding of the cytoplasmic domain receptor to FADD; c) contacting the agent to be screened with the receptor bound support of step b) under conditions favoring binding of the cytoplasmic domain to the receptor to FADD; d) detecting the presence of any complex formed between Fas receptor and FADD to form Fas receptor-FADD complex; and e) the absence of complex being indicative that the agent inhibits binding of FADD to the Fas receptor and therefore is an inhibitor of Fas receptor mediated cellular function. This invention also provides the agents detected by these methods and the use of these agents in the therapeutic methods described herein. As is apparent to those of skill in the art, the above compositions can be combined with instructions for use to provide a kit for a commercially available screen.

The compositions provided herein also are useful to modulate the Fas receptor pathway and cellular functions associated with this pathway, for example, preventing or inhibiting Fas regulated apoptosis or growth and differentiation of cells. As used herein, the term "Fas-receptor mediated or modulated cellular function" is to include any cellular response or function which has been linked to the binding of Fas or Fas/TNF receptor complex to its extracellular and/or intracellular ligand.

When applied to apoptosis, the terms "preventing" or "inhibiting" are intended to mean a reduction in cell death or a prolongation in the survival time of the cell. They also are intended to mean a diminution in the appearance or a delay in the appearance of morphological and/or biochemical changes normally associated with apoptosis. Thus, this invention provides compositions and methods to increase survival time and/or survival rate of a cell or population of cells which, absent the use of the method, would normally be expected to die. Accordingly, it also provides compositions and methods to prevent or treat diseases or pathological conditions associated with unwanted cell death in a subject.

Apoptosis can be assessed by the use of fluorescent DNA-staining dyes to reveal nuclear morphology and by transmission electron microscopy. For propidium iodide staining, cells can be grown on 22 mm$^2$ No. 1 glass coverslips (Corning) placed in 35 mm wells of a 6-well culture dish (Costar). Following treatment with TNF, anti-Fas cycloheximide (CHX), or no treatment, medium can be removed and the wells rinsed twice with phosphate buffered saline (PBS), fixed in 100% methanol at –20° C. for 10 minutes, washed three times with PBS, and stained at room temperature for 10 minutes in a 100 $\mu$g/ml solution or propidium iodide (Sigma) made in PBS. The coverslips are then washed three times with PBS, blotted dry and mounted onto glass slides using Vectashield mounting medium for fluorescence (Vector Laboratories). Cells can be stained using acridine orange (sigma) by preparing a wet mount of 30 $\mu$l of a cell suspension at a density of approximately 3×10$^5$ cell/ml mixed with 5 $\mu$l of a 100 $\mu$g/ml acridine orange solution made in PBS. Both propidium iodide-stained MCF7 and acridine orange-stained BJAB nuclei were visualized by fluorescence microscopy using a FITC range barrier filter cube. Laser-scanning confocal microscopy was performed using the Bio-Rad MRC 600 confocal microscope and digitized images obtained were artificially colorized.

For electron microscopy, cells can be fixed and processed as per standard electron microscopy procedures.

When a function associated with the Fas receptor mediated pathway should be augmented, nucleic acid molecules coding for FADD can be inserted into a Fas$^+$ cell, such as a T cell, using an appropriate pharmaceutical vector. Alternatively, when a function, associated with the Fas receptor pathway should be inhibited or prevented, a nucleic acid coding for anti-FADD antibody fragment, a dominant inhibitory FADD polypeptide fragment, or anti-sense FADD RNA can be introduced into a Fas$^+$ cell using an appropriate pharmaceutical vector.

When practiced in vivo, the compositions and methods are particularly useful for modulating or regulating Fas receptor induced function in a subject or an individual suffering from or predisposed to suffer from receptor-related disfunction, CD4 T cell depletion associated with HIV infection. When the animal is an experimental animal such as a mouse, this method provides a powerful assay to screen for new drugs that may be used alone or in combination with this invention to ameliorate or reduce the symptoms and infections associated with Fas-related-disfunction such as CD4 T cell depletion.

As used herein, the term "administering" for in vivo purposes means providing the subject with an effective amount of the nucleic acid molecule, polypeptide or antibody, effective to modulate Fas-related function of the target cell. Methods of administering pharmaceutical compositions are well known to those of skill in the art and include, but are not limited to, microinjection, intravenous or parenteral administration. The compositions are intended for topical, oral, or local administration as well as intravenously, subcutaneously, or intramuscularly. Administration can be effected continuously or intermittently throughout the course of treatment. Methods of determining the most effective means and dosage of administration are well known to those of skill in the art and will vary with the vector used for therapy, the polypeptide or protein used for therapy, the purpose of the therapy, the target cell being treated, and the subject being treated. Single or multiple administrations can be carried out with the dose level and pattern being selected by the treating physician.

The compositions also can be administered to subjects or individuals susceptible to or at risk of developing a Fas receptor induced disease. In one embodiment, the composition can be administered to a subject susceptible to the disease or pathology to maintain lymphocyte cell function such as antibody production. In these instances, a "prophylactically effective amount" of the composition is administered which is defined herein to be an amount that is effective to maintain the targeted cellular function, such as lymphocyte function, at an acceptable level.

It should be understood that by preventing or inhibiting Fas receptor related disfunction in a subject or individual, the compositions and methods of this invention also provide methods for treating, preventing or ameliorating the symptoms associated with a Fas receptor mediated disease.

When practiced in vivo, the compositions and methods are particularly useful for maintaining T cell viability and function in a subject or an individual suffering from or predisposed to suffer from abnormal lymphocyte death. When the animal is an experimental animal such as a simian (using SIV), this method provides a powerful assay to screen for new drugs that may be used alone or in combination with this invention to ameliorate or reduce the symptoms and opportunistic infections associated with HIV infection or AIDS.

This invention also is particularly useful to ward off lymphocyte death or immunosuppression in AIDS patients. By preventing or inhibiting apoptosis, not only is cell death prevented but functionality, e.g., immuno-proliferative capacity, is restored to the cell and a responsive immune system is retained or regained. Accordingly, the compositions and methods of this invention are suitably combined with compositions and methods which prevent or inhibit HIV infectivity and replication.

The method can also be practiced ex vivo using a modification of the method described in Lum et al. (1993) *Bone Marrow Transplantation* 12:565–571. Generally, a sample of cells such as bone marrow cells or MLC can be removed from a subject or animal using methods well known to those of skill in the art. An effective amount of FADD or anti-FADD nucleic acid is added to the cells and the cells are cultured under conditions that favor internalization of the nucleic acid by the cells. The transformed cells are then returned or reintroduced to the same subject or animal (autologous) or one of the same species (allogeneic) in an effective amount and in combination with appropriate pharmaceutical compositions and carriers.

As used herein, the term "administering" for in vivo and ex vivo purposes means providing the subject with an effective amount of the nucleic acid molecule or polypeptide effective to prevent or inhibit apoptosis of the target cell. Methods of administering pharmaceutical compositions are well known to those of skill in the art and include, but are not limited to, microinjection, intravenous or parenteral administration. The compositions are intended for topical, oral, or local administration as well as intravenously, subcutaneously, or intramuscularly. Administration can be effected continuously or intermittently throughout the course of treatment. Methods of determining the most effective means and dosage of administration are well known to those of skill in the art and will vary with the vector used for therapy, the polypeptide or protein used for therapy, the purpose of the therapy, the target cell being treated, and the subject being treated. Single or multiple administrations can be carried out with the dose level and pattern being selected by the treating physician. For example, the compositions can be administered prior to a subject already suffering from a disease or condition that is linked to apoptosis. In this situation, an effective "therapeutic amount" of the composition is administered to prevent or at least partially arrest apoptosis and the accompanying pathology such as immunosuppression in HIV infected individuals.

However, the compositions can be administered to subjects or individuals susceptible to or at risk of developing apoptosis-related disease to prevent pathological cell death. In one embodiment, the composition can be administered to a subject susceptible to HIV-related lymphocyte disfunction to maintain lymphocyte cell function and viability. In these a "prophylactically effective amount" of the composition is administered to maintain cellular viability and function at a level near to the pre-infection level.

It should be understood that by preventing or inhibiting unwanted cell death in a subject or individual, the compositions and methods of this invention also provide methods for treating, preventing or ameliorating the symptoms associated with a disease characterized by apoptosis of cells. Such diseases include but are not limited to AIDS, acute and chronic inflammatory disease, leukemia, myocardial infarction, stroke, traumatic brain injury, neural and muscular degenerative diseases, aging, tumor induced-cachexia and hair loss.

This invention also provides vector and protein compositions useful for the preparation of medicaments which can be used for preventing or inhibiting apoptosis, maintaining cellular function and viability in a suitable cell or for the treatment of a disease characterized by the unwanted death of target cells.

It is to be understood that while the invention has been described in conjunction with the above embodiments, that the foregoing description and the following examples are intended to illustrate and not limit the scope of the invention. Other aspects, advantages and modifications within the scope of the invention will be apparent to those skilled in the art to which the invention pertains.

EXPERIMENTAL PROCEDURES

Experiment I

The following yeast two-hybrid system was used and constructed as follows. The cytoplasmic domains of Fas, Fas-FD8, TNRF-1, Δ-TNFR-1, CD40, and CD28 were obtained by PCR and cloned in-frame, as confirmed by sequencing, into the GAL4 DNA binding domain (GAL4bd) vector pAS1CYH2. Full-length A20 and B94 were similarly cloned into the bait vector. GAL4bd-Fas was cotransformed with a prey plasmid containing a human B-cell cDNA expression library fused to the GAL4 activation domain (GAL4ad) in the pACT plasmid. A more detailed account of the plasmids used in the procedure for the yeast two-hybrid system can be found in Hu et al. (1994) *J. Biol. Chem.* 269:30069–30072.

Figure 1:
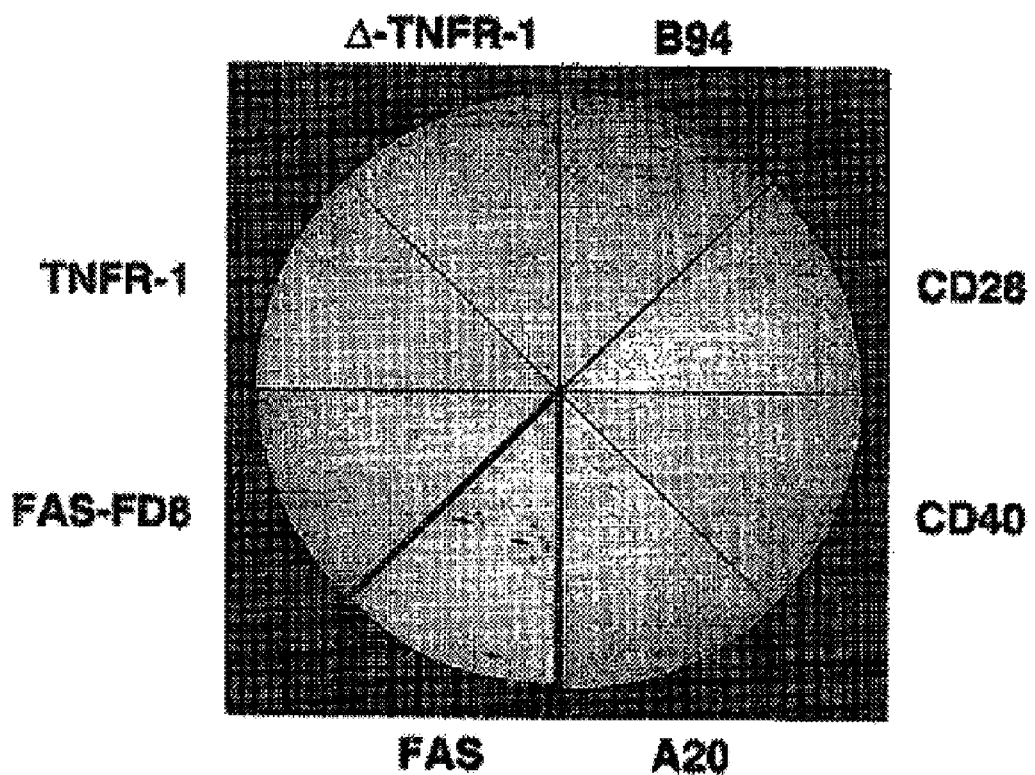
FIG. 1 shows that FADD specifically interacts with the cytoplasmic domain of Fas in yeast. β-galactosidase filter assays performed on Y190 yeast expressing the GAL4 activation domain-FADD fusion protein and indicated heterologous GAL4 DNA binding domain fusion proteins.

The yeast two-hybrid system was used to screen for proteins that interact with the cytoplasmic domain of Fas. An expression vector was constructed by fusing the GAL4 DNA-binding domain to the cytoplasmic tail of the human Fas antigen (GAL4bd-Fas). This bait plasmid was cotransformed in yeast with a prey plasmid containing a human B-cell cDNA expression library fused to the GAL4-activation domain. Seventeen positive clones were obtained from $2 \times 10^6$ transformants screened. To determine the specificity of interaction, plasmids containing the activation domain fusion proteins were recovered from the putative positive clones and cotransformed with GAL4bd-Fas and control heterologous baits. Two clones (8 and 15) were found to interact with the GAL4. DNA-binding domain fusion protein containing the cytoplasmic domain of wild-type Fas and not the functionally inactive deletion mutant, Fas-FD8 (Itoh et al., 1993) or the indicated heterologous baits (FIG. 1).

Experiment II
Isolation of the Sequence

Double-stranded plasmid template was sequenced on both strands by the dideoxy chain termination method using modified T7 DNA polymerase (Sequenase, U.S. Biochemical Corp.). Manual sequencing was confirmed by subsequent automated sequencing. Network BLAST searches were conducted using the NCBI-online service. Sequences were compared using the MogAlign (DNASTAR) software.

A random-promed cDNA library was constructed in the pcDNA1 vector (Invitrogen) from TNF/cycloheximide treated human umbilical vein endothelial cell poly(A)+ RNA. $5 \times 10^5$ colonies were screened with a $^{32}P$ random-labeled XhoI restriction fragment of the yeast prey plasmid encoding GAL4ad-FADD (clone 15) using standard techniques (Sambrook et al. (1989) supra.

Figure 3A:
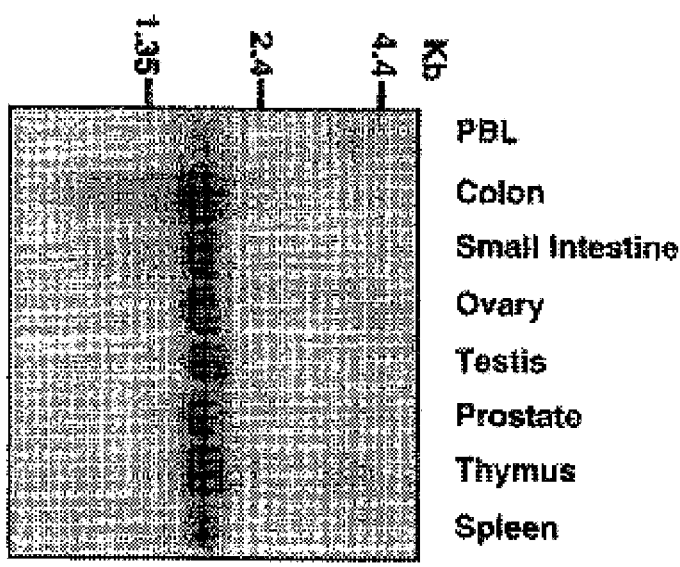
FIGS. 3A and 3B show that FADD is expressed in a variety of tissues and developmental stages.
Figure 3B:
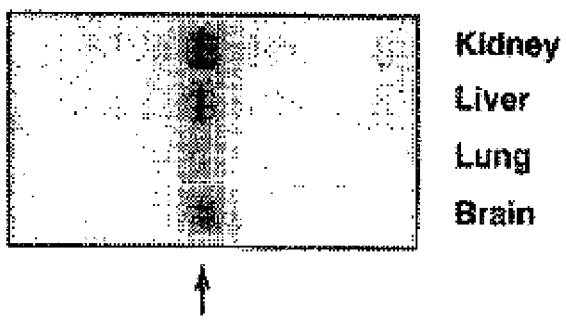

As noted in Experiment I, clones 8 and 15 isolated by the yeast two-hybrid screen were found to contain overlapping sequence fused to the GAL4 activation domain in the same reading frame. To obtain a full-length coding sequence, a human umbilical vein endothelial cell (HUVEC) library was screened with a cDNA insert obtained from clone 15. Two independent clones yielded a 1.6 kb cDNA containing an open reading frame that begins with an initiator methionine conforming to Kozak's consensus (Kozak, 1989) and that ends 625 nucleotides later at an Opal codon. Given the presence of an in-frame stop codon 130 base pairs upstream of the initiator methionine and the size of the transcript (~1.6 kb; FIG. 3), it is likely that FIG. 2A represents the full-length coding sequence. This gene encodes a novel protein of 208 amino acids with a predicted molecular weight of 23.3 kDa, designated FADD.

A BLAST search revealed that residues 111–170 of FADD matched residues 233–292 of rat Fas antigen (rFas, p=0.0012) and shared 27% identity (51% of the amino acids were conserved). This region in the cytoplasmic domain of rFas corresponds to the death domain, a region of homology shared by both Fas and TNFR-1 that signals cell death (Tartaglia et al., 1993; Itoh et al., 1993).

Dependent upon the alignment and boundaries selected, the death domains of FADD, Fas, and TNFR-1 share 25–30% identity (FIG. 2B). When conservative amino acid substitutions are included, the homologies approach 50%. These numbers are consistent with those previously reported for the death domain homology between TNFR-1 and Fas (Tartaglia et al. (1993) supra Itoh et al. (1993) supra). Interestingly, $V^{121}$ of FADD is aligned and conserved with $V^{238}$ of Fas, which when altered to an asparagine, abolishes the cell killing activity of Fas and in mice, is responsible for the lymphoproliferation (Lpr) phenotype (Watanabe-Fukunaga et al., 1992). A corresponding inactivating mutation also exists in TNFR-1, $L^{351} \rightarrow N^{351}$ (Tartaglia et al., 1993)

Experiment III
Northern Blot Analysis of Tissues

Adult and fetal human multiple tissue Northern blots (CLONTECH) were hybridized, according to the manufacturer's instructions using radiolabeled cDNA insert obtained from an XhoI digestion of the yeast prey plasmid encoding GAL4ad-FADD (clone 15).

Northern blot analysis revealed that FADD is constitutively expressed in a wide array of fetal and adult human tissues (FIG. 3). The mRNA transcript is approximately 1.6 kb, consistent with the size of the cDNA clones isolated from the HUVEC library.

Experiment IV

FADD was cloned into pcDNA3 (Invitrogen) in which an HA-epitope tag (YPYDVPDYA) (SEQ ID No:7) had previously been placed downstream of the cytomegalovirus promoter/enhancer (pcDNA3 HA-FADD). In addition, an AU1-epitope (DTYRYI) (SEQ ID NO:8) tagged FADD was made with PCR primers encoding the epitope and using the FADD cDNA as template (pcDNA3 AU1-FADD). FLAG (DYKDDDDK) (SEQ ID NO:9)-tagged constructs of Fas and mutants were also made in pcDNA3 using full-length Fas as a template. The 5° FLAG PCR primer was engineered to encode a FLAG epitope 5 amino acids downstream of the putative signal sequence site of Fas and is as follows: AAG CCT GGT ACC ATG CTG GGC ATC TGG ACC CTC CTA CCT CTG GTT CTT ACG TCT GTT GCT AGA TTA TCG TCC AAA GAC TAC AAG GAC GAC GAT GAC AAG AGT GTT AAT GCC CAA GTC (SEQ ID NO:10). The amplified products were then cloned into the KpnI/XhoI site of pcDNA3. pcDNA3 AU1-FADDmt and pcDNA3 FLAG-Fas-LPR were made by site-directed mutagenesis using a two-step PCR protocol as described in Higuchi, R. et al.

(1988) *Nucleic Acids Res.* 16:7351–7367. The $V^{121} \rightarrow N^{121}$ and $V^{238} \rightarrow N^{238}$ mutations, respectively, were confirmed by sequence analysis.

Experiment V

GST Fusion Protein Expression and In Vitro Binding Assay

The cytoplasmic domains of Fas, Fas-FD5, Fas-FD8, and TNFR-1 were amplified by PCR using appropriate templates and primers and cloned in-frame into pGSTag using the method disclosed in Ron, D. et al. (1992) *Biotechnigues* 13:866–869. Fas-LPft was made by site-directed mutagenesis using a two-step PCR protocol (Higuchi et al., 1988) and cloned into pGSTag. The $V^{238} \rightarrow N^{238}$ mutation was confirmed by sequence analysis. The pGSTag constructs were then transformed into the *E. coli* strain BL21(DE3) pLysS (Studier, 1991). GST and GST fusions were prepared using published procedures (Studier, (1991) *J. Mol. Biol.* 219:37–44) and the recombinant proteins immobilized onto glutathione-agarose beads as described Harper, J. W. et al. (1993) *Cell* 75:805–816.

Labeled FADD was prepared by in vitro transcription/translation using TNT T7 coupled reticulocyte lysate system from Promega according to the manufacturer's instructions, using pcDNA3 HA-FADD as template.

Following translation, equal amounts of total $^{35}$S-labeled reticulocyte lysate were diluted into 150 μl GST binding buffer (50 mM Tris, pH 7.6, 120 mM NaCl, 1% Brij) and incubated for 2 hrs. at 4° C. with the various GST fusion proteins complexed to beads, following which the beads were pelleted by pulse centrifugation, washed 3 times in GST buffer, boiled in SDS-sample buffer and resolved on a 10% SDS-acrylamide gel. Bound proteins were visualized following autoradiography at –80° C.

Lysates of FADD or FADDmt-transfected 293T cells were processed as above except that the GST binding buffer also had 10% glycerol and a protease inhibitor cocktail. For some experiments, the complexed GST beads were dissociated by boiling in PBS+1% SDS, diluted tenfold in PBS containing 1% deoxycholate and subsequently subjected to immunoprecipitation analysis.

Experiment VI

Transfection, metabolic labeling and immunoprecipitation analysis was performed as described in O'Rourke, K. M. et al. (1992) *J. Biol. Chem.* 267:24921–24924. For re-immunoprecipitation analysis, the initial immune complex was dissociated by boiling in PBS+1% SDS, diluted tenfold in PBS containing 1% deoxycholate and subjected to a second round of immunoprecipitation analysis.

Figure 4A:
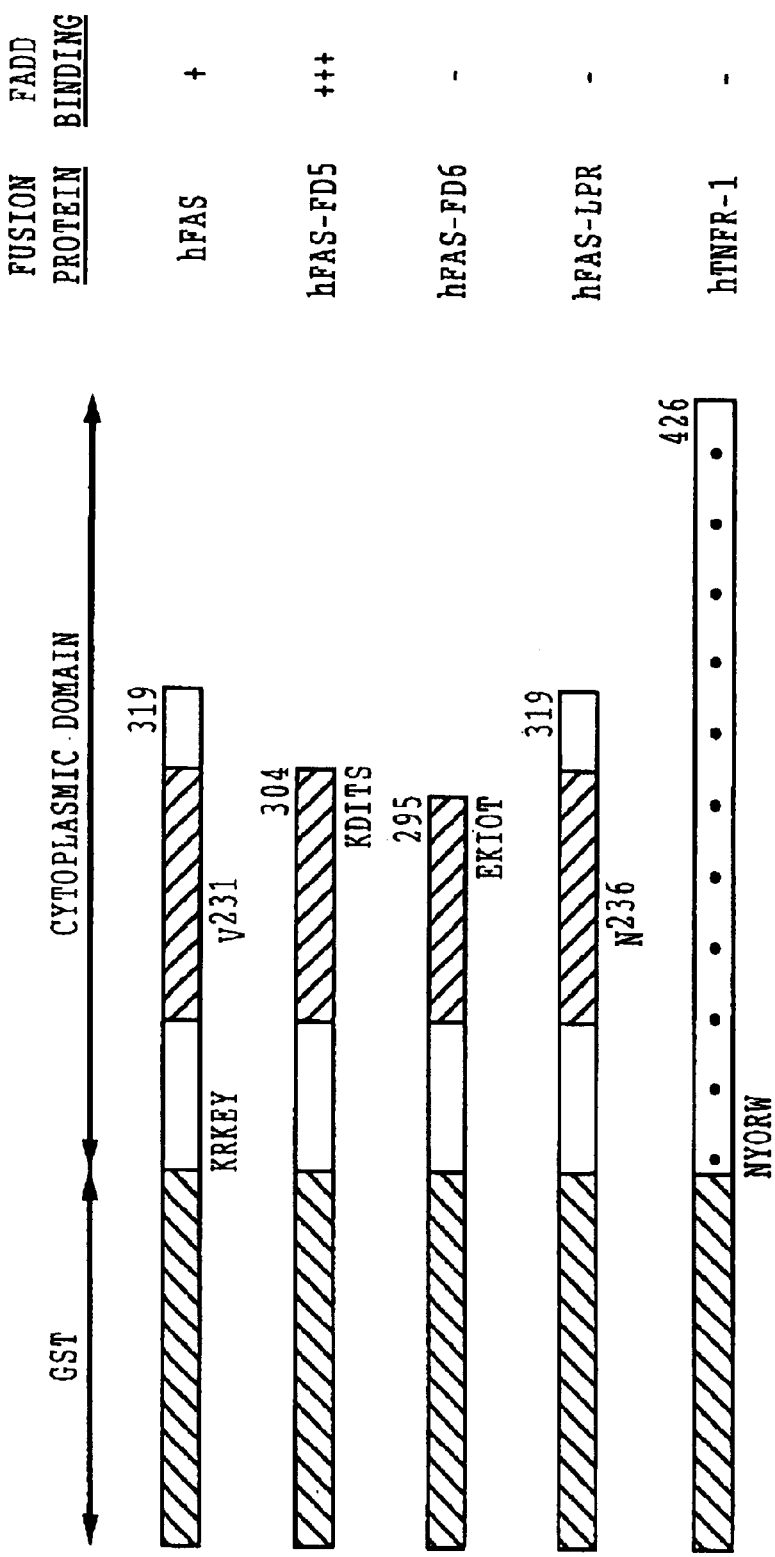
FIGS. 4A through 4C show the specific interaction of GST-Fas and GST-Fas-FDS with in vitro translated FADD and FADD expressed in transfected 293T cells.
Figure 4B:
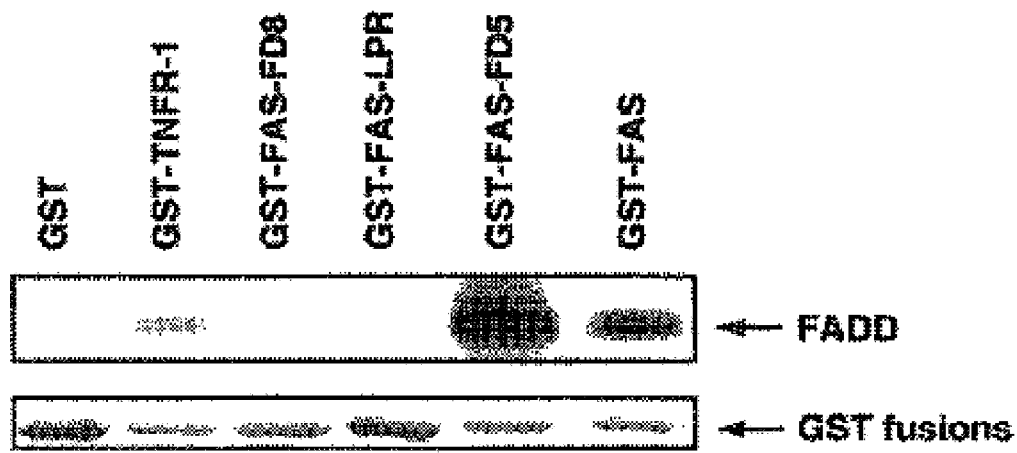
Figure 4C:
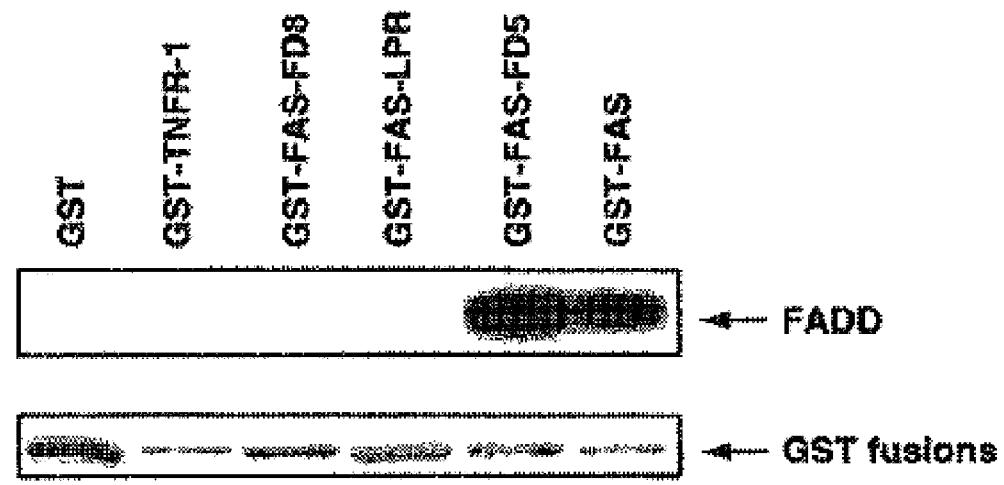

To confirm the interaction observed in yeast, radiolabeled in vitro translated FADD was precipitated with various GST fusion proteins immobilized on glutathione-Sepharose beads (FIGS. 4A, B). As predicted, FADD specifically associated with GST-Fas but, not GST, GST-Fas-FD8, or GST-Fas-LPR, which contains the cytoplasmic domain of the functionally inactive point mutant of Fas (Itoh et al., 1993). A very weak interaction was observed between FADD and TNFR-1. Interestingly, relative to its association with GST-Fas, FADD strongly interacted with GST-Fas-FD5, which is a 15 amino acid C-terminal deletion mutant of Fas possessing enhanced killing activity (Itoh et al., 1993). Similar results were obtained when detergent lysates of 293T cells expressing FADD were precipitated with the various GST fusion proteins (FIG. 4C).

Experiment VII

Functional Assay and Immunocytochemistry

Stable CrmA and vector transfectants (BJAB) were described previously (Tewari et al. (1995) supra.). For transient transfections, 5×10$^6$ cells were electroporated at 220V, 960 μF in 0.4 cm cuvettes (Bio-Rad) using 20 μg of pCMV β-galactosidase ±30 μg of pcDNA3 AU-FADD. After 12 hours, cells were cytocentrifuged, fixed with 1% paraformaldehyde, permeabilized with 0.1% Triton/PBS, blocked with horse serum, and incubated with rabbit anti-β-galactosidase (1:200 dilution, Cappel) for 1 hour. The cells were subsequently washed with PBS, incubated with biotinylated anti-rabbit antibody (1:200 dilution, Vector Laboratories) for 20 min., washed with PBS, and incubated with Avidin-FITC (1:100 dilution, Vector Laboratories) for 20 min. The nuclei were stained with a 10 μg/ml solution of propidium iodide (Sigma) for 10 minutes. Cells were visualized by fluorescence microscopy using aFITC range barrier filter cube. For graphical data, at least 100 β-galactosidase positive cells were counted for each transfection (n=3) and designated as apoptotic or non-apoptotic. Immunostaining for AU1-FADD was done as above except that cells were fixed in 100% methanol at –20ΣC for 10 min., the primary antibody was against the AU1 epitope (1:50 dilution, Babco) and the secondary antibody was a FITC conjugated anti-mouse Ab (Sigma).

Coimmunoprecipitation of FADD and Fas

To demonstrate the interaction of FADD and Fas in vivo, 293T cells were transiently transfected with HA-epitope tagged FADD (HA-FADD) and FLAG-epitope tagged Fas (FLAG-Fas) and mutants (FIG. 5). Expression of the FLAG-tagged constructs was shown by immunoprecipitation with an anti-FLAG (α-FLAG) antibody (FIG. 5B). Likewise, immunoprecipitation with anti-HA (α-HA) antibody showed expression of HA-FADD, and as expected, FLAG-Fas and FLAG-Fas-FD5 individually coprecipitated, while the functionally inactive mutants, FLAG-Fas-FD8 and FLAG-Fas-LPR did not (FIG. 5C). The α-HA immunoprecipitates were dissociated and subjected to a second round of immunoprecipitation with α-FLAG antibody. Consistent with results of the primary immunoprecipitation (with α-HA), a double immunoprecipitation with α-HA followed by α-FLAG, confirmed the presence of FLAG-Fas and FLAG-Fas-FD5 in the original immune complexes (FIG. 5D).

The Death Domain of FADD Interacts With the Death Domain of Fas

Previous studies have reported that the death domains of TNFR-1 and Fas self-associate (Boldin et al., (1995) supra and Wallach et al. (1994) supra). The two clones (8 and 15) isolated in the two-hybrid screen described above (using the cytoplasmic domain of Fas as bait) did not contain various portions of the N-terminus of wild-type FADD. The shortest of the two, clone 8, is missing the N-terminal 40 amino acids, suggesting that the C-terminal half of FADD, which contains the death domain, is interacting with the cytoplasmic tail of Fas. More specifically, our results show that FADD interacts with death domain of Fas, since it fails to associate with Fas-LPR and Fas-FD8, a point mutant and deletion mutant, respectively, of the Fas death domain.

Thus, it is reasonable to propose that the death domain of FADD is interacting with its homologous counterpart in Fas. To test this hypothesis, a point mutant of FADD (FADDmt) was engineered in which $V^{121}$ is altered to an asparagine. This mutation corresponds to the inactivating Lpr mutation ($V^{238} \rightarrow N^{238}$) of Fas and the $L^{351} \rightarrow N^{351}$ mutation of TNFR-1. 293T cells were transiently transfected with expression constructs containing AU1-epitope tagged FADD (AU1-FADD) and AU1-FADDmt. Detergent lysates were prepared and subsequently precipitated with GST, GST-Fas and GST-Fas-LPR immobilized on glutathione-Sepharose beads (FIG. 6). As predicted, AU1-FADD bound GST-Fas and not GST or GST-Fas-LPR, while in contrast, AU1-FADDmt failed to bind any of the GST fusions. Taken together, these results show that a death domain to death domain interaction is responsible for the association of FADD and Fas.
Overexpression of FADD Initiates Apoptosis Which is Suppressed by CrmA.

To study the functional role of FADD the B-cell lymphoma cell line, BJAB was chosen. This is an ideal cell system to study proteins involved in Fas signal transduction because BJAB cells are exquisitely sensitive to anti-Fas antibody induced cell death in the absence of protein synthesis inhibitors (Tewari et al. (1995) supra). Two well characterized clonal cell lines of BJAB were used in this study: one expresses CrmA, which has been shown to potently block Fas-mediated cell death, while the other is a corresponding vector control cell line (Tewari et al. (1995) supra). To help identify transiently transfected cells, the plasmid was co-transfected with an expression construct encoding: β-galactosidase (pCMV β-gal). As expected, over 90' of the cells that expressed β-galactosidase also expressed the protein of interest as confirmed by immunostaining.

CrmA-expressing and vector control BJAB cell lines were transfected with the pCMV β-gal reporter in the presence or absence of an equimolar amount of an expression construct encoding AU1-epitope tagged FADD (pcDNA3 AU1-FADD). As expected, expression of β-galactosidase alone in both the CrmA and vector clones did not induce apoptotic cell death as assessed by propidium iodide staining of nuclei of β-galactosidase positive cells (FIG. 7A, upper panels). In contrast, however, the vector control cell line co-transfected with PCMV β-gal and pcDNA3 AU1-FADD exhibited prominent apoptotic morphology including chromatin condensation and cellular shrinkage (FIG. 7A, lower left panel). More importantly, FADD-induced apoptosis, like Fas-induced apoptosis, was inhibited in the CrmA-expressing line (FIG. 7A, lower right panel). A graphical representation of this data is shown in. FIG. 7B. In the vector control lines, over 90% of the transfected cells expressing FADD were apoptotic while less than 10% exhibited similar morphology in the corresponding CrmA-expressing lines. As a control, expression of AU1-TRAF1 and HA-CD40bp revealed less than 10% apoptotic morphology in either the CrmA or vector cell lines. Immunostaining for AU1-FADD with an anti-AU1 antibody is shown in FIG. 7C. At present, it is unclear whether FADD is a soluble cytoplasmic protein or associated with cellular membranes.

Experimental Summary

Using the yeast two-hybrid screen, FADD was identified as,a novel protein that associates specifically with the cytoplasmic domain of Fas (FIG. 1). A BLAST search using the amino acid sequence of FADD revealed a stretch of 80 amino acids that were significantly homologous to the death domain of Fas (FIG. 2B). When the region of FADD was masked, the remaining sequences did not match any proteins in the database. Interestingly, BLAST searches using the death domains of FADD, Fas and TNFR-1 revealed a significant homology to the family of ankyrins (p<0.001 for all three death domains). More specifically, the respective death domains aligned with approximately 80 amino acids of the negative regulatory domain of ankyrin. A previous study reported that this region of ankyrin is homologous to the cytoplasmic domain of TNFR-1 (Peters et al. (1993) *Semin. in Hematol.* 30:85–118), corroborating this observation. Why ankyrin contains a "death domain" remains unclear, but presumably this region is acting as a protein interaction domain.

In vitro and in vivo studies show that FADD specifically associates with the death domain of Fas, confirming the results of the yeast interaction assay. FADD failed to interact with Fas-LPR and Fas-FD8, a non-signaling point mutant and deletion mutant, respectively, of the Fas death domain. Interestingly, upon deletion of the negative regulatory domain of Fas, an enhanced interaction with FADD was observed. Hence, a correlation exists between the cell-killing activity of the various Fas mutants and their association with FADD (FIG. 5A). A weak association between FADD and TNFR-1 was observed in vitro (FIG. 4). In addition, β-galactosidase filter assays of yeast cotransformed with GAL4bd-Fas and GAL4ad-FADD turned blue within 1 hr, while those cotransformed with GAL4bd-TNFR-1 and GAL4ad-FADD turned blue overnight (the other cotransformed heterologous baits remained unchanged). If the weak interaction between FADD and TNFR-1 observed in yeast and in vitro proves to be significant, this would correlate with the relative potencies of Fas-dependent cell death and TNF-dependent cytotoxicity (Clement, M-V. et al. (1994) *J. Exp. Med.* 180:557–567).

Having shown that FADD specifically binds the death domain of Fas, the next step was to identify the corresponding interaction-domain in Fas. Previous studies have shown that death domains have a propensity to self-associate (Boldin et al. (1995) supra). It was thus reasonable to propose that the death domain of FADD was interacting with its homologous counterpart in Fas. As predicted, a point mutation in the death domain of FADD abrogated its association with Fas (FIG. 6). These results support a model in which a death domain to death domain interaction is responsible for the binding of FADD to Fas (FIG. 8).

Once the in vitro and in vivo association of FADD and Fas was established, the next step was to determine a functional role for this novel Fas binding protein. BJAB cells transiently transfected with AU1-FADD undergo apoptosis within 12 hours—a time frame similar to Fas-induced killing (FIGS. 7A and 7B). Previous studies showed that CrmA is a potent inhibitor of Fas-induced cell death (Tewari et al. (1995) supra). Likewise, CrmA suppressed FADD-induced cell death (FIGS. 7A and 7B). These functional studies, together with the biochemical data, suggests that FADD is likely a component of the Fas-signal transduction machinery.

It is to be understood that while the invention has been described in conjunction with the above embodiments, that the foregoing description and the examples are intended to illustrate and not limit the scope of the invention. Other aspects, advantages and modifications within the scope of the invention will be apparent to those skilled in the art to which the invention pertains.

Throughout this application, various publications, patents and published patent applications are referred to by an identifying citation. The disclosures of these publications, patents and published patent applications are hereby incorporated by reference into this application to more fully describe the state of the art to which this invention pertains.

What is claimed is:

1. An isolated nucleic acid molecule comprising a sequence encoding a polypeptide comprising amino acid residues 111 to 170 of SEQ ID NO:2.

2. The isolated nucleic acid molecule of claim 1 comprising nucleotide 460 to 639 of SEQ ID NO:1.

* * * * *